(12) United States Patent
Burkholz et al.

(10) Patent No.: US 12,097,336 B2
(45) Date of Patent: *Sep. 24, 2024

(54) MEDICAL DEVICES, SYSTEMS AND METHODS UTILIZING PERMANENT MAGNET AND MAGNETIZABLE FEATURE

(71) Applicant: Becton, Dickinson and Company, Franklin Lakes, NJ (US)

(72) Inventors: Jonathan Karl Burkholz, Salt Lake City, UT (US); Siddarth Shevgoor, Mission Viejo, CA (US); Edward G. Henderson, Draper, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/380,387

(22) Filed: Oct. 16, 2023

(65) Prior Publication Data

US 2024/0033481 A1 Feb. 1, 2024

Related U.S. Application Data

(63) Continuation of application No. 15/604,244, filed on May 24, 2017, now Pat. No. 11,826,522.
(Continued)

(51) Int. Cl.
*A61M 25/01* (2006.01)
*A61B 5/06* (2006.01)
(Continued)

(52) U.S. Cl.
CPC ......... *A61M 25/0127* (2013.01); *A61B 5/062* (2013.01); *A61B 8/0841* (2013.01);
(Continued)

(58) Field of Classification Search
CPC .......... A61M 25/0127; A61M 25/0102; A61M 25/02; A61M 25/0618; A61M 25/065;
(Continued)

(56) References Cited

U.S. PATENT DOCUMENTS

| 4,161,943 A | 7/1979 | Nogier |
| 5,000,912 A | 3/1991 | Bendel et al. |

(Continued)

FOREIGN PATENT DOCUMENTS

| CN | 201138912 Y | 10/2008 |
| DE | 3742298 A1 | 6/1989 |

(Continued)

OTHER PUBLICATIONS

"Final Office Action in U.S. Appl. No. 15/154,348 dated Mar. 22, 2019, 9 pages".
(Continued)

*Primary Examiner* — Sean A Frith
(74) *Attorney, Agent, or Firm* — Servilla Whitney LLC

(57) ABSTRACT

Systems, methods and devices are described including a medical device subassembly including a magnetic feature. Systems include such a catheter adapter subassembly or needle subassembly or guidewire introducer subassembly and a wire including a magnetic feature, and relative movement of the catheter adapter subassembly or needle subassembly or guidewire introducer subassembly and the wire can be determined using a magnetometer.

24 Claims, 20 Drawing Sheets

Related U.S. Application Data

(60) Provisional application No. 62/344,162, filed on Jun. 1, 2016.

(51) Int. Cl.
| | |
|---|---|
| *A61B 8/00* | (2006.01) |
| *A61B 8/08* | (2006.01) |
| *A61B 34/20* | (2016.01) |
| *A61M 25/02* | (2006.01) |
| *A61M 25/06* | (2006.01) |
| *A61M 25/09* | (2006.01) |
| *A61M 39/10* | (2006.01) |

(52) U.S. Cl.
CPC ............ *A61B 8/4254* (2013.01); *A61B 34/20* (2016.02); *A61M 25/0102* (2013.01); *A61M 25/02* (2013.01); *A61M 25/0618* (2013.01); *A61M 25/065* (2013.01); *A61M 25/09041* (2013.01); *A61M 39/10* (2013.01); *A61B 2034/2051* (2016.02); *A61M 2025/0266* (2013.01); *A61M 2039/1077* (2013.01)

(58) Field of Classification Search
CPC ............ A61M 25/09041; A61M 39/10; A61M 2025/0266; A61M 2039/1077; A61B 34/20; A61B 5/062; A61B 8/0841; A61B 8/4254; A61B 2034/2051
See application file for complete search history.

(56) References Cited

U.S. PATENT DOCUMENTS

| | | | |
|---|---|---|---|
| 5,154,179 A | 10/1992 | Ratner | |
| 5,215,528 A | 6/1993 | Purdy et al. | |
| 5,279,044 A | 1/1994 | Bremer | |
| 5,359,992 A | 11/1994 | Hori et al. | |
| 5,431,640 A | 7/1995 | Gabriel | |
| 5,461,311 A | 10/1995 | Nakazato et al. | |
| 5,558,651 A | 9/1996 | Crawford et al. | |
| 5,728,079 A | 3/1998 | Weber et al. | |
| 5,817,017 A | 10/1998 | Young et al. | |
| 5,955,881 A | 9/1999 | White et al. | |
| 6,171,297 B1 | 1/2001 | Pedersen | |
| 6,216,026 B1 | 4/2001 | Kuhn | |
| 6,216,029 B1 | 4/2001 | Paltieli | |
| 6,263,230 B1 | 7/2001 | Haynor et al. | |
| 6,337,627 B1 | 1/2002 | Von Gutfeld et al. | |
| 6,432,036 B1 | 8/2002 | Kim | |
| 6,475,226 B1 | 11/2002 | Belef et al. | |
| 6,537,232 B1 | 3/2003 | Kucharczyk et al. | |
| 6,733,458 B1 | 5/2004 | Steins et al. | |
| 7,244,234 B2 | 7/2007 | Ridley et al. | |
| 7,932,718 B1 | 4/2011 | Wiegert | |
| 7,935,080 B2 | 5/2011 | Howell et al. | |
| 8,152,724 B2 | 4/2012 | Ridley et al. | |
| 8,496,592 B2 | 1/2013 | Ridley et al. | |
| 8,388,541 B2 | 3/2013 | Messerly et al. | |
| 8,425,425 B2 | 4/2013 | Hagy et al. | |
| 8,761,862 B2 | 6/2014 | Ridley et al. | |
| 8,900,151 B2 | 12/2014 | Ridley et al. | |
| 9,351,704 B2 | 5/2016 | Ridley et al. | |
| 9,433,396 B2 | 9/2016 | Ridley et al. | |
| 9,492,097 B2 | 11/2016 | Wilkes et al. | |
| 10,178,984 B2 | 1/2019 | Hagy et al. | |
| 10,537,302 B2 | 1/2020 | Hagy et al. | |
| 10,610,195 B2 | 4/2020 | Hagy et al. | |
| 11,045,165 B2 | 6/2021 | Hagy et al. | |
| 11,129,589 B1 | 9/2021 | Hagy et al. | |
| 11,129,590 B1 | 9/2021 | Hagy et al. | |
| 11,134,913 B1 | 10/2021 | Hagy et al. | |
| 11,134,914 B1 | 10/2021 | Hagy et al. | |
| 11,207,050 B1 | 12/2021 | Hagy et al. | |
| 11,826,522 B2 * | 11/2023 | Burkholz | A61M 39/10 |
| 2002/0042581 A1 | 4/2002 | Cervi | |
| 2002/0052546 A1 | 5/2002 | Frantz et al. | |
| 2003/0100829 A1 | 5/2003 | Zhong | |
| 2003/0117135 A1 | 6/2003 | Martinelli | |
| 2004/0167506 A1 | 8/2004 | Chen | |
| 2004/0249428 A1 | 12/2004 | Wang et al. | |
| 2005/0004417 A1 | 1/2005 | Nelson et al. | |
| 2005/0027198 A1 | 2/2005 | Couvillon, Jr. | |
| 2005/0096589 A1 | 5/2005 | Shachar | |
| 2005/0107738 A1 | 5/2005 | Slater et al. | |
| 2005/0165301 A1 | 7/2005 | Smith et al. | |
| 2005/0203333 A1 | 9/2005 | Dailey et al. | |
| 2005/0215885 A1 | 9/2005 | Lee | |
| 2006/0264914 A1 | 11/2006 | Furst et al. | |
| 2007/0016006 A1 | 1/2007 | Shachar | |
| 2007/0016131 A1 | 1/2007 | Munger et al. | |
| 2007/0049846 A1 | 3/2007 | Bown et al. | |
| 2007/0088197 A1 | 4/2007 | Garibaldi | |
| 2007/0167747 A1 | 7/2007 | Borgert | |
| 2007/0255211 A1 | 11/2007 | Young | |
| 2008/0006280 A1 | 1/2008 | Aliberto et al. | |
| 2008/0132911 A1 | 6/2008 | Sobe | |
| 2008/0204004 A1 | 8/2008 | Anderson | |
| 2008/0237367 A1 | 10/2008 | McNichols et al. | |
| 2008/0281391 A1 | 11/2008 | Macadam | |
| 2009/0012517 A1 | 1/2009 | De La Rama et al. | |
| 2009/0032499 A1 | 2/2009 | Tenne et al. | |
| 2010/0036238 A1 | 2/2010 | Neidert et al. | |
| 2010/0217275 A1 | 8/2010 | Carmeli et al. | |
| 2010/0228119 A1 | 9/2010 | Brennan et al. | |
| 2010/0230862 A1 | 9/2010 | Arney et al. | |
| 2010/0305402 A1 | 12/2010 | Shachar | |
| 2011/0092870 A1 | 4/2011 | Jarrell | |
| 2011/0196397 A1 | 8/2011 | Frantz et al. | |
| 2011/0267043 A1 | 11/2011 | Dolsak | |
| 2012/0016316 A1 | 1/2012 | Zhuang et al. | |
| 2012/0041297 A1 | 2/2012 | Mcgary | |
| 2012/0046664 A1 | 2/2012 | Mcguckin, Jr. et al. | |
| 2012/0075649 A1 | 3/2012 | Tse | |
| 2012/0095319 A1 | 4/2012 | Kondrosky et al. | |
| 2012/0116294 A1 | 5/2012 | Boenig et al. | |
| 2012/0143029 A1 | 6/2012 | Silverstein et al. | |
| 2013/0023758 A1 | 1/2013 | Fabro | |
| 2013/0075649 A1 | 3/2013 | Wang | |
| 2013/0123704 A1 | 5/2013 | Bierman et al. | |
| 2013/0131547 A1 | 5/2013 | Hardert et al. | |
| 2013/0263668 A1 | 10/2013 | Hyun et al. | |
| 2013/0303886 A1 | 11/2013 | Ludwin et al. | |
| 2014/0018665 A1 | 1/2014 | Meredith | |
| 2014/0031674 A1 | 1/2014 | Newman et al. | |
| 2014/0046261 A1 * | 2/2014 | Newman | A61B 5/062 |
| | | | 604/158 |
| 2014/0107475 A1 | 4/2014 | Cos et al. | |
| 2014/0180328 A1 | 6/2014 | Vaccaro et al. | |
| 2014/0187916 A1 | 7/2014 | Clark | |
| 2014/0187917 A1 | 7/2014 | Clark | |
| 2014/0253270 A1 | 9/2014 | Nicholls et al. | |
| 2014/0257080 A1 * | 9/2014 | Dunbar | A61B 5/062 |
| | | | 600/409 |
| 2014/0276539 A1 | 9/2014 | Allison et al. | |
| 2014/0296694 A1 | 10/2014 | Jaworski | |
| 2015/0080710 A1 | 3/2015 | Henkel et al. | |
| 2015/0306351 A1 | 10/2015 | Bornhoft | |
| 2015/0320977 A1 | 11/2015 | Vitullo et al. | |
| 2015/0359991 A1 | 12/2015 | Dunbar et al. | |
| 2016/0029998 A1 * | 2/2016 | Brister | A61B 8/0833 |
| | | | 600/424 |
| 2016/0220314 A1 | 8/2016 | Huelman et al. | |
| 2016/0331470 A1 | 11/2016 | Sato | |
| 2016/0361519 A1 | 12/2016 | Teoh et al. | |
| 2017/0232204 A1 | 8/2017 | Knapp et al. | |
| 2017/0325713 A1 | 11/2017 | Burkholz et al. | |
| 2017/0325714 A1 | 11/2017 | Sonderegger | |
| 2017/0326342 A1 | 11/2017 | Ma et al. | |
| 2017/0347913 A1 | 12/2017 | Isaacson et al. | |
| 2017/0347914 A1 | 12/2017 | Isaacson et al. | |
| 2017/0348509 A1 | 12/2017 | Burkholz et al. | |
| 2017/0348510 A1 | 12/2017 | Shevgoor et al. | |

(56) References Cited

U.S. PATENT DOCUMENTS

| | | |
|---|---|---|
| 2017/0348511 A1 | 12/2017 | Burkholz et al. |
| 2020/0121278 A1 | 4/2020 | Hagy et al. |

FOREIGN PATENT DOCUMENTS

| | | |
|---|---|---|
| EP | 0320623 A1 | 11/1988 |
| EP | 2730306 A1 | 5/2014 |
| JP | H0327774 A | 2/1991 |
| JP | H08509141 A | 10/1996 |
| JP | H11500939 A | 1/1999 |
| JP | H11319106 A | 11/1999 |
| JP | 3786312 B2 | 6/2006 |
| JP | 2006520645 A | 9/2006 |
| JP | 2008512270 A | 4/2008 |
| JP | 2009505744 A | 2/2009 |
| JP | 2013526961 A | 6/2013 |
| JP | 2014501143 A | 1/2014 |
| JP | 2015518752 A | 7/2015 |
| JP | 2016059549 A | 4/2016 |
| WO | 9640347 A1 | 12/1996 |
| WO | 02/083208 A2 | 10/2002 |
| WO | 2009061860 A1 | 5/2009 |
| WO | 2009152486 A1 | 12/2009 |
| WO | 2011069525 A1 | 6/2011 |
| WO | 2012032881 A1 | 3/2012 |
| WO | 2013034175 A1 | 3/2013 |
| WO | 2013142386 A1 | 9/2013 |
| WO | 2014052894 A2 | 4/2014 |
| WO | 2014062728 A1 | 4/2014 |
| WO | 2016187456 A1 | 11/2016 |

OTHER PUBLICATIONS

"Final Office Action in U.S. Appl. No. 15/154,353 dated Jul. 12, 2019, 12 pages".
"Final Office Action in U.S. Appl. No. 15/154,353 dated Jun. 24, 2020, 12 pages".
"Final Office Action in U.S. Appl. No. 15/170,497 dated Jun. 23, 2020, 44 pages".
"Final Office Action in U.S. Appl. No. 15/170,497 dated Sep. 16, 2019, 47 pages".
"Final Office Action in U.S. Appl. No. 15/170,518 dated Nov. 7, 2019, 32 pages".
"Final Office Action in U.S. Appl. No. 15/170,518, mailed on Jul. 8, 2021, 49 pages".
"Final Office Action in U.S. Appl. No. 15/170,531 dated Mar. 3, 2021".
"Laser Welding in Medical Device Technology [online].", Rofin, May 8, 2015 [retrieved on Jan. 26, 2019]. Retrieved from the Internet :<URL: https://web .archive.org/web/20150508080208/ https://www.rofin.com/en/markets/medical-device-technology/laser-welding/>.
"Non-Final Office Action in U.S. Appl. No. 15/154,348 dated Jun. 7, 2018, 14 pages".
"Non-Final Office Action in U.S. Appl. No. 15/154,353 dated Mar. 17, 2020, 12 pages".
"Non-Final Office Action in U.S. Appl. No. 15/154,353 dated Mar. 19, 2019, 12 pages".
"Non-Final Office Action in U.S. Appl. No. 15/170,497 dated Jan. 24, 2020, 47 pages".
"Non-Final Office Action in U.S. Appl. No. 15/170,497, mailed on Dec. 31, 2020, 37 pages".
"Non-Final Office Action in U.S. Appl. No. 15/170,518 dated Feb. 19, 2021, 21 pages".
"Non-Final Office Action in U.S. Appl. No. 15/170,531 dated Sep. 6, 2019, 41 pages".
"Non-Final Office Action in U.S. Appl. No. 15/170,531, mailed on Sep. 18, 2020, 39 pages".
"PCT International Preliminary Report on Patentability & Written Opinion in PCT/US2017/034517, dated Dec. 4, 2018", 8 pgs.
"PCT International Preliminary Report on Patentability and Written Opionin in PCT/US2017/034515, dated Dec. 4, 2018", 8 pgs.
"PCT International Preliminary Report on Patentability in PCT/US2017/031566 dated Nov. 22, 2018, 11 pages".
"PCT International Preliminary Report on Patentability in PCT/US2017/031572 dated Nov. 22, 2018, 8 pages".
"PCT International Preliminary Report on Patentability in PCT/US2017/033984 dated Dec. 13, 2018, 9 pages".
"PCT International Search Report and Written Opinion in PCT/US2017/031569 dated Aug. 28, 2017, 17 pages".
"PCT International Search Report and Written Opinion in PCT/US2017/033984, dated Aug. 2, 2017", 15 pgs.
"PCT International Search Report and Written Opinion in PCT/US2017/033985 dated Sep. 25, 2017, 16 pages".
"PCT International Search Report and Written Opinion in PCT/US2017/033986 dated Aug. 28, 2017, 17 pages".
"PCT International Search Report and Written Opinion in PCT/US2017/033988 dated Aug. 24, 2017, 17 pages".
"PCT International Search Report and Written Opinion in PCT/US2017/034515 dated Aug. 2, 2017, 15 pages".
"PCT International Search Report and Written Opinion in PCT/US2017/034517 dated Aug. 2, 2017, 15 pages".
"PCT International Search Report in PCT/US2017/031572 dated Aug. 24, 2017, 14 pages".
"PCT IPRP in S/N PCT/US2017/033988, issued Dec. 4, 2018", 8 pgs.
Bhattacharya, Deepamala , ALNICO [online], Chemistry Learner, May 31, 2014 [retrieved on Mar. 2, 2020], Retrieved from the Internet: <URL: https://web.archive.Org/web/20140531135446/http://www.chemistrylearner.com/alnico.html>.
Honnegowda, Lakshmisha , et al., "Security Enhancement for Magnetic Data Transaction in Electronic Payment and Healthcare Systems [online]", IACSIT International Journal of Engineering and Technology, Apr. 2013 [retrieved on Sep. 5, 2019], vol. 5, No. 2.
Nave, R. , "Ferromagnetism [online], Georgia State University, HyperPhysics, Jul. 1, 2006 [retrieved on Oct. 12, 2018].", Retrieved from the internet: <URL: https://web.archive.org/web/20060701023036/http://hyperphysics.bhyastr.gsu.edu/hbase/Solids/ferro.html>, 1 page.

* cited by examiner

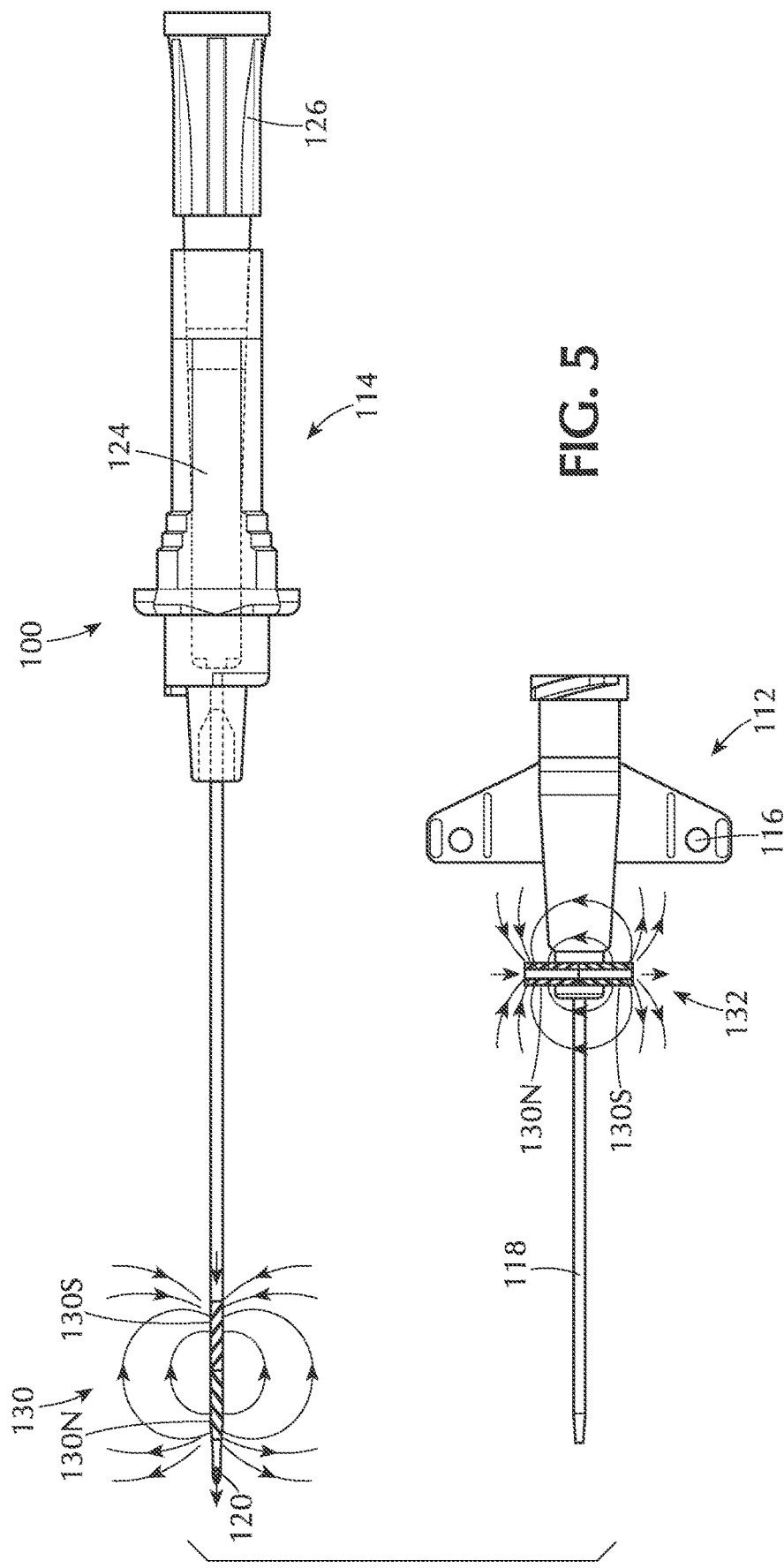

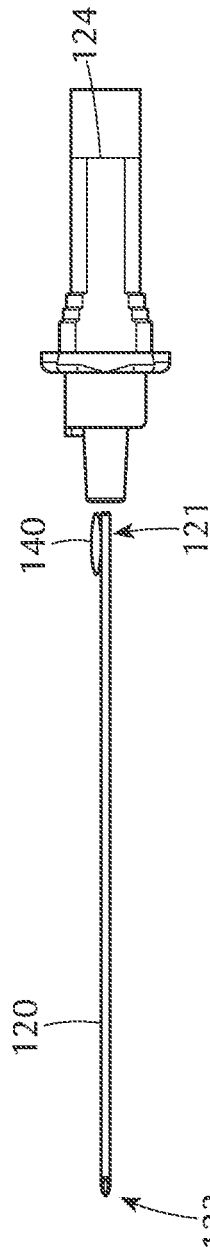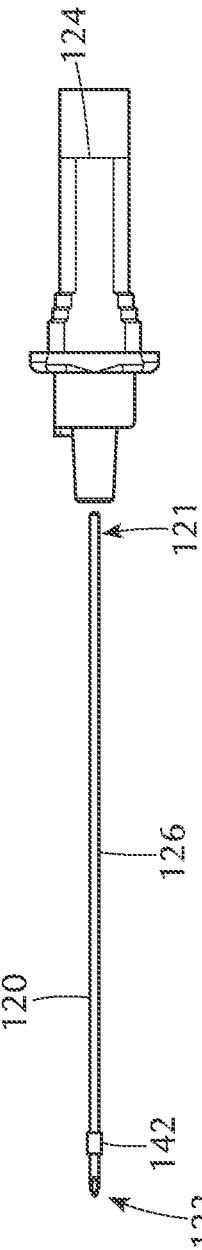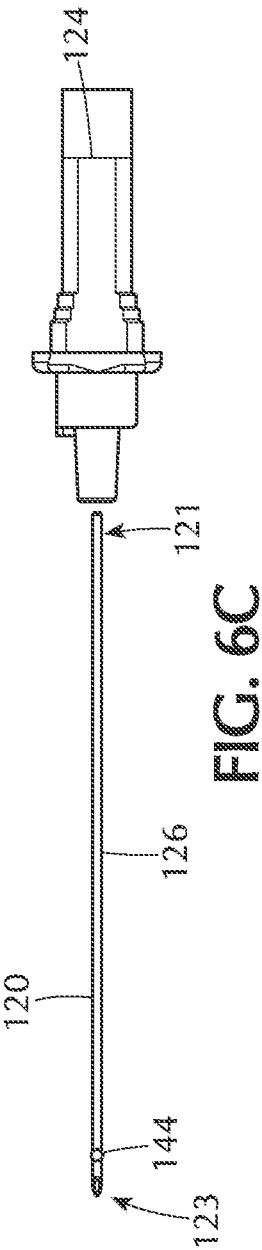

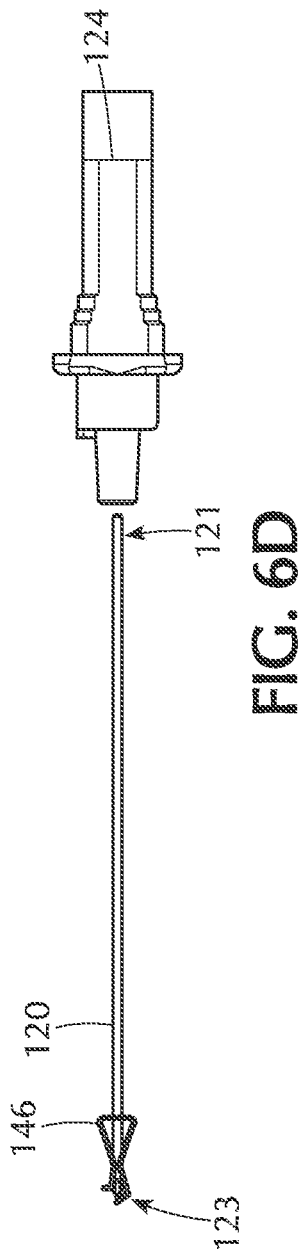
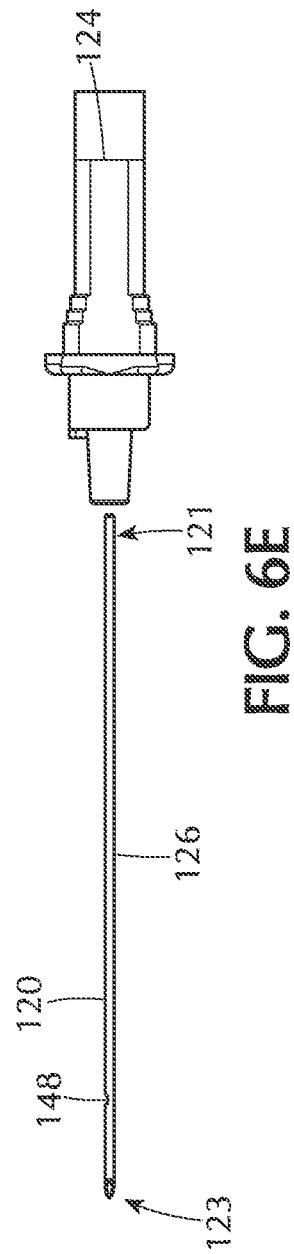

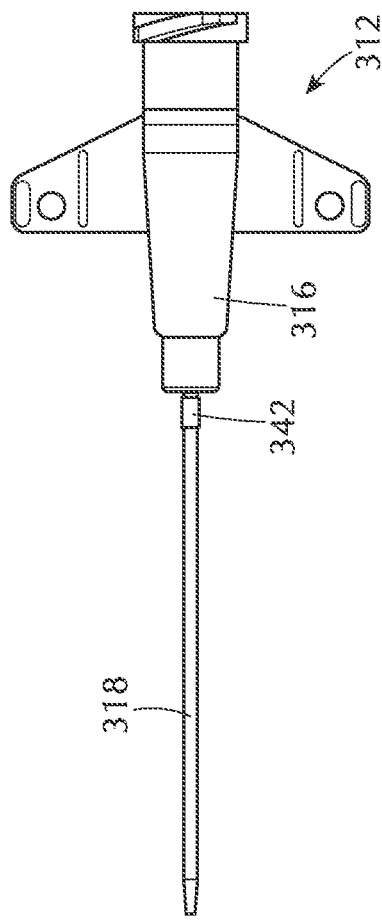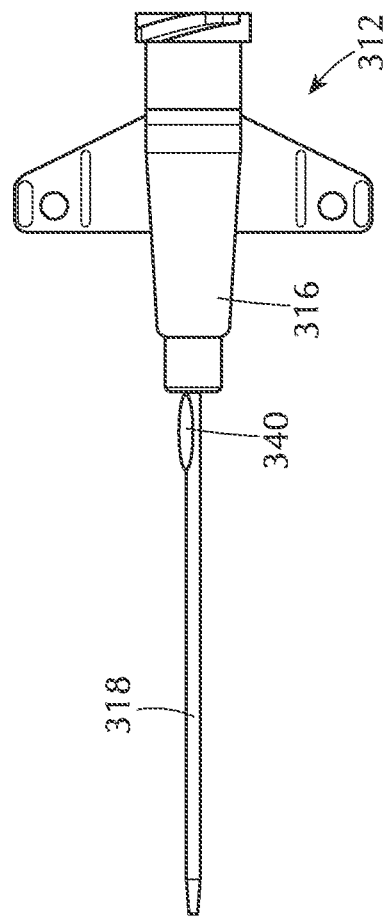

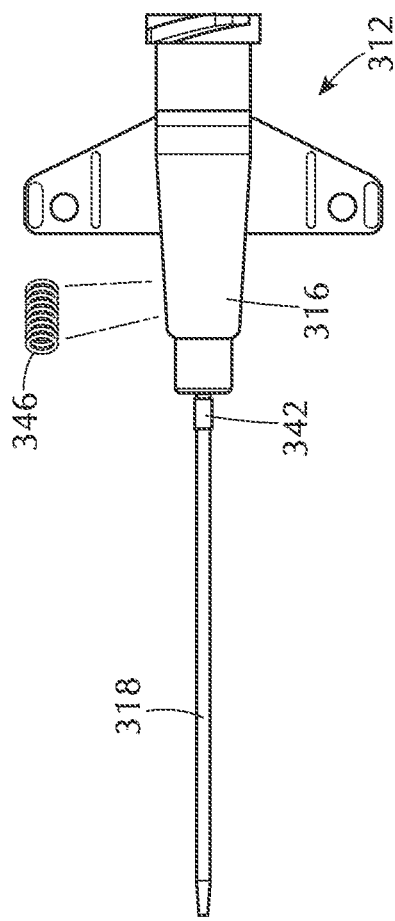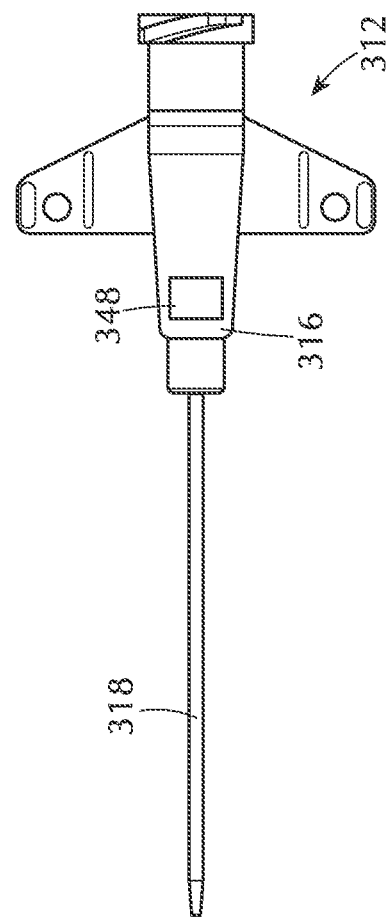

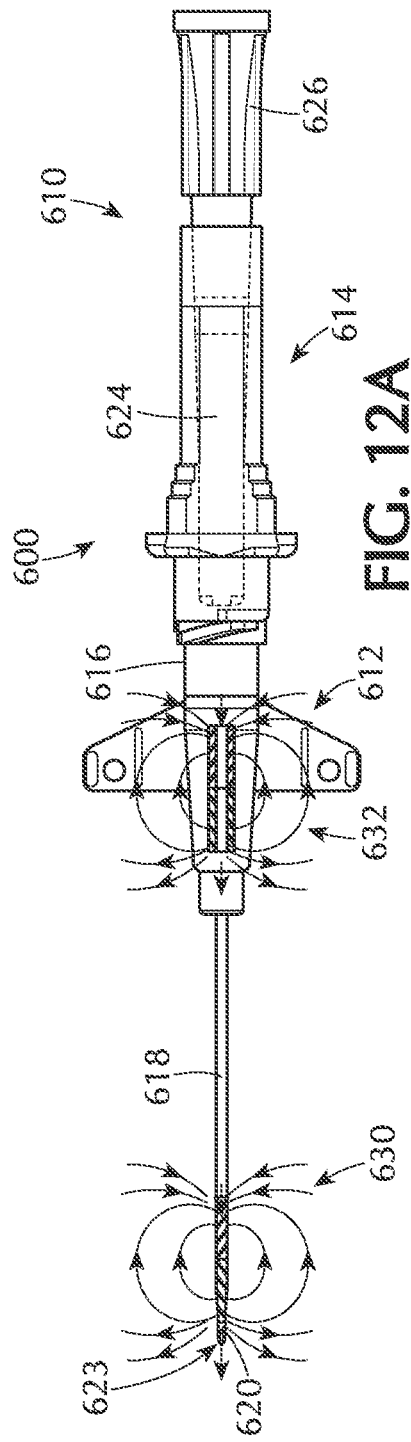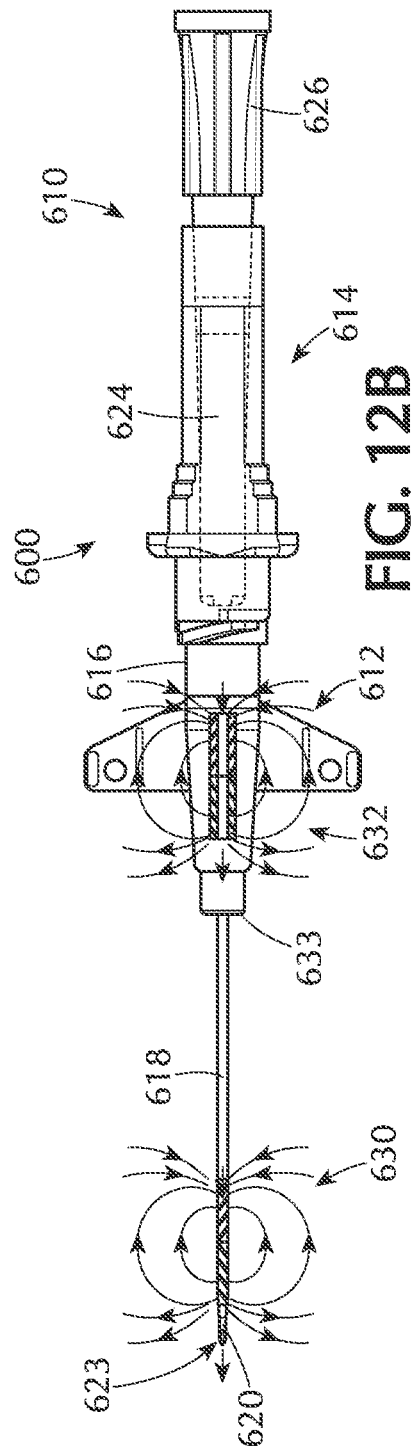

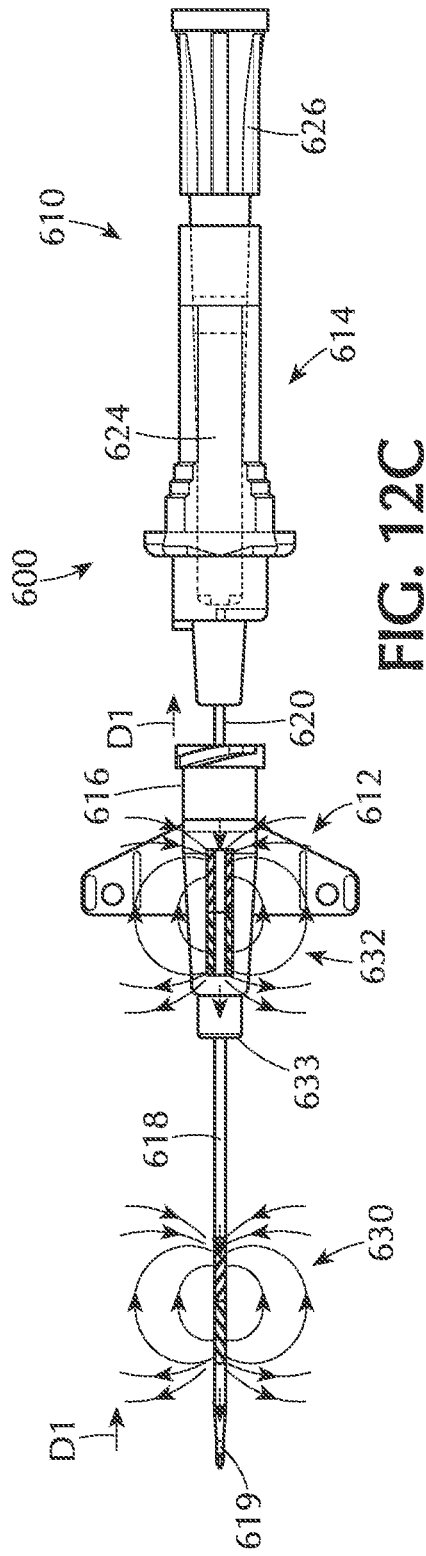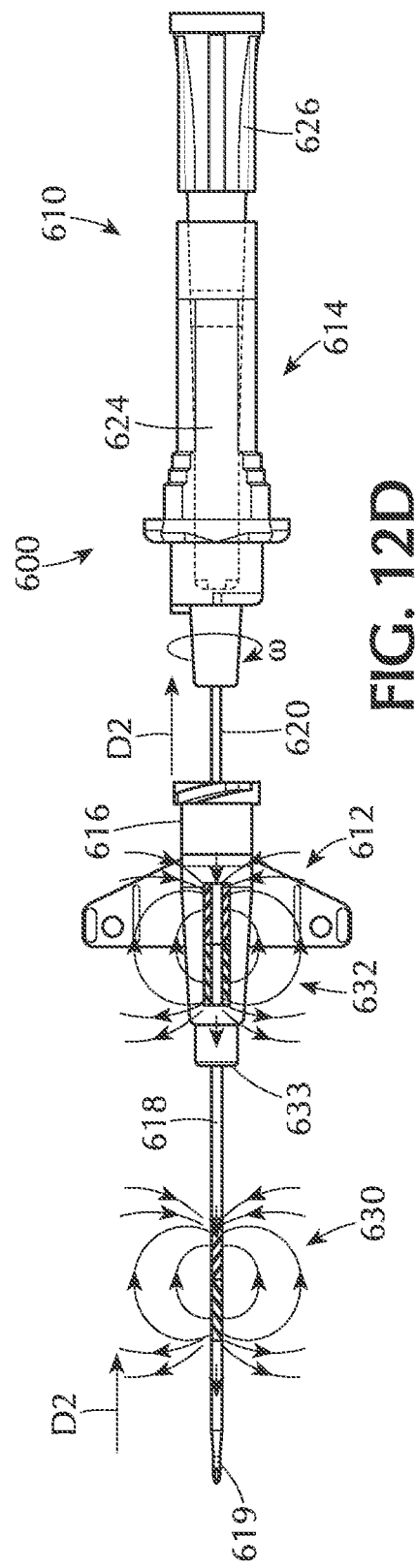

MEDICAL DEVICES, SYSTEMS AND METHODS UTILIZING PERMANENT MAGNET AND MAGNETIZABLE FEATURE

CROSS-REFERENCE TO RELATED APPLICATION

This application claims priority under 35 U.S.C. § 119(e) to U.S. Provisional Application No. 62/344,162, filed Jun. 1, 2016, and is a continuation of U.S. patent application Ser. No. 15/604,244, filed on May 24, 2017, the disclosures of which are incorporated herein by reference in their entirety.

FIELD

Principles and embodiments of the present disclosure relate generally to devices, systems and methods including a permanent magnet and a magnetizable feature.

BACKGROUND

Traditionally, penetration of a needle, guidewire, stylet or other medical device through skin tissue to reach the vein during catheter insertion is invisible to clinicians. For this reason, they must rely on their first-hand experience with device insertion in combination with tactile sense to successfully identify the location of the vein or other location with the body. This may be a difficult task when attempting to access a small vein in a deep location under the skin, or a remote location within a patient's body such as the pleural cavity, increasing risk of excess pain and/or injury to the patient.

Emerging procedural guidance systems utilize a combination of ultrasound and magnetic technologies to provide visualization of subdermal anatomy and device position in the in-plane and out-of-plane orientations. This combination of ultrasound and magnetic methods also allows for the projection or anticipation of the insertion device position relative to the patient's anatomy, and thereby improves the likelihood of successfully accessing the vasculature or other part of the body and completing the invasive procedure.

For needles, one leading technology targets the cannula as the portion of the invasive device for magnetization, while another leading technology uses a permanent magnet located on the needle hub of the device. Although a permanent magnet offers a more reliable magnetic field as it is not subject to the variation of the clinician magnetizing the needle at the point of use, it does rely more on a calculated projection of the needle tip location. The system that relies on magnetizing the cannula prior to insertion can more reliably measure the actual tip location, but this method is subject to variability on consistently magnetizing the cannula as it relies on the clinician to place the needle into a magnetic device to magnetize the needle. Both of these systems utilize a magnetic field generated by a portion of the cannula subassembly, and therefore, it is not able to measure or predict relative motion between the needle hub and catheter adapter subassemblies. Understanding the relative position and motion of these two subassemblies can be used to inform a clinician of procedurally important states of the insertion process, such as when the needle tip reaches the vein, when the catheter tip reaches the vein, when the catheter is advanced to cover the needle tip ("hooding the catheter") and thereby safe for further advancement. Similar considerations apply with respect to insertion of medical wires such as stylets and guidewires, which can be used in combination with a needle subassembly or catheter subassembly, as it would be desirable to understand the relative position of a wire and a medical device subassembly. It would be desirable to provide medical devices, system and methods that could be used with devices, systems and methods to provide improved visualization during penetration of a wire through a patient's skin tissue.

SUMMARY

Various embodiments are listed below. It will be understood that the embodiments listed below may be combined not only as listed below, but in other suitable combinations in accordance with the scope of the disclosure. In one embodiment, a medical device comprises a catheter adapter subassembly and a wire subassembly including a wire, wherein one of the catheter adapter subassembly and the wire subassembly includes a permanent magnet element, and the other of the catheter adapter subassembly and the wire subassembly includes a magnetizable feature to permit measurement of relative motion of the wire subassembly and the catheter adapter subassembly. Another embodiment pertains to a medical device comprising a needle subassembly and a wire subassembly including a wire, wherein one of the needle subassembly and the wire subassembly includes a permanent magnet element, and the other of the needle subassembly and the wire subassembly includes a magnetizable feature to permit measurement of relative motion of the wire subassembly and the needle subassembly.

In another embodiment, a guidewire introducer assembly comprises a guidewire introducer subassembly having at least one end and a guidewire extending from the at least one end of the guidewire introducer, wherein one of the guidewire introducer subassembly and the guidewire includes a permanent magnet element, and the other of the guidewire introducer subassembly and the guidewire includes a magnetizable feature.

Another embodiment pertains to a system for determining relative position of a catheter adapter subassembly and wire subassembly comprising a catheter having a catheter distal tip and a wire having a wire distal tip; a permanent magnet element associated with one of the catheter adapter subassembly and wire subassembly; a magnetizable feature associated with the other of the catheter adapter subassembly and the wire subassembly; and magnetometers positioned with respect to the catheter adapter subassembly and the wire subassembly, the magnetometers configured to determine relative movement of the catheter adapter subassembly and wire subassembly. Another embodiment pertains to a system for determining relative position of a needle subassembly and wire subassembly comprising a needle having a needle distal tip and a wire having a wire distal tip; a permanent magnet element associated with one of the needle subassembly and wire subassembly; a magnetizable feature associated with the other of the needle subassembly and the wire subassembly; and magnetometers positioned with respect to the needle subassembly and the wire subassembly, the magnetometers configured to determine relative movement of the needle subassembly and wire subassembly.

Another embodiment pertains to a method for determining a relative position of a catheter tip and a wire tip, the method comprising providing a catheter adapter subassembly including catheter and a wire subassembly including a wire, the catheter having a catheter distal tip and the wire having a wire distal tip; associating a permanent magnet element with one of the catheter and the wire; associating a magnetizable feature with the other of the catheter and the wire; obtaining a measured position of the permanent magnet; obtaining a measured position of the magnetizable feature to obtain a calculated position of the catheter distal tip and a calculated position of the wire distal tip; and comparing the calculated position of the catheter distal tip with the calculated position of the wire distal tip to determine the relative position of the catheter distal tip and the wire distal tip. Another embodiment pertains to a method for determining a relative position of a wire tip and a needle cannula tip, the method comprising providing a needle subassembly including needle and a wire subassembly including a wire, the needle having a needle distal tip and the wire having a wire distal tip; associating a permanent magnet element with one of the needle and the wire; associating a magnetizable feature with the other of the needle and the wire; obtaining a measured position of the permanent magnet; obtaining a measured position of the magnetizable feature to obtain a calculated position of the needle distal tip and a calculated position of the wire distal tip; and comparing the calculated position of the needle distal tip with the calculated position of the wire distal tip to determine the relative position of the needle distal tip and the wire distal tip.

BRIEF DESCRIPTION OF THE DRAWINGS

FIG. 5 shows the catheter assembly of FIG. 4 with the needle subassembly and catheter adapter subassembly separated;

FIG. 6A is a top plan view showing a portion of a needle subassembly with the needle disconnected from the needle chamber and a magnetic feature;

FIG. 6B is a top plan view showing a portion of an alternative embodiment of a needle subassembly with the needle disconnected from the needle chamber and a magnetic feature;

FIG. 6C is a top plan view showing a portion of an alternative embodiment of a needle subassembly with the needle disconnected from the needle chamber and a magnetic feature;

FIG. 6D is a top plan view showing a portion of an alternative embodiment of a needle subassembly with the needle disconnected from the needle chamber and a magnetic feature;

FIG. 6E is a top plan view showing a portion of an alternative embodiment of a needle subassembly with the needle disconnected from the needle chamber and a magnetic feature;

FIG. 10A is a top plan view of a catheter adapter subassembly according to an embodiment;

FIG. 10B is a top plan view of a catheter adapter subassembly according to an embodiment;

FIG. 10C is a top plan view of a catheter adapter subassembly according to an embodiment;

FIG. 10D is a top plan view of a catheter adapter subassembly according to an embodiment;

FIG. 12A is a top plan view of an embodiment of a catheter assembly;

FIG. 12B shows the catheter assembly of FIG. 12A in a first position;

FIG. 12C shows the catheter assembly of FIG. 12A with the needle subassembly and catheter adapter subassembly moved with respect to each other;

FIG. 12D shows the catheter assembly of FIG. 12A with the needle subassembly and catheter adapter subassembly moved further apart with respect to each other;

DETAILED DESCRIPTION

Figure 1:
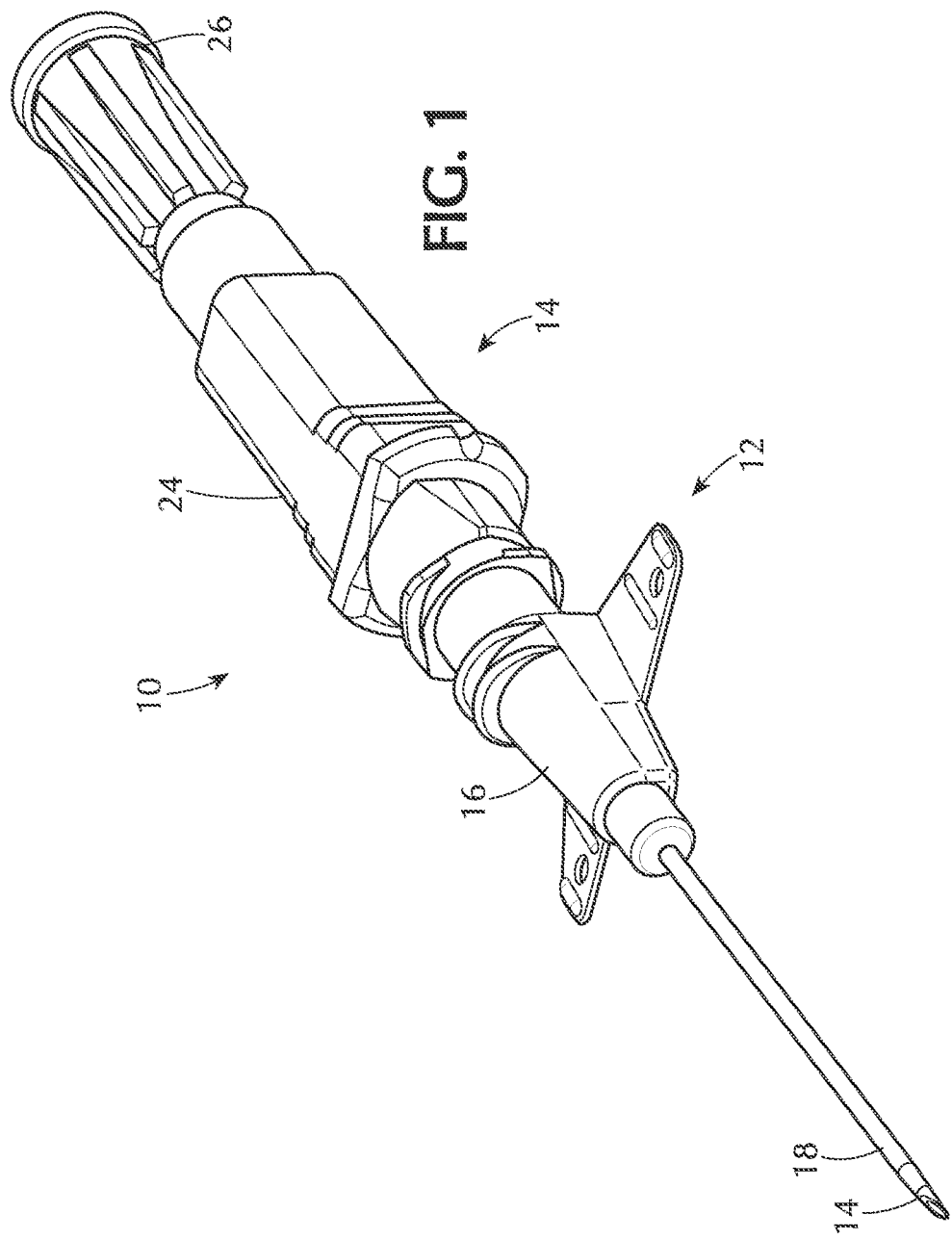
FIG. 1 is a perspective view of a catheter assembly that can be utilized according to an embodiment.

Before describing several exemplary embodiments, it is to be understood that the disclosure is not limited to the details of construction or process steps set forth in the following description. The disclosure is capable of other embodiments and of being practiced or being carried out in various ways.

Reference throughout this specification to "one embodiment," "certain embodiments," "various embodiments," "one or more embodiments" or "an embodiment" means that a particular feature, structure, material, or characteristic described in connection with the embodiment is included in at least one embodiment. Thus, the appearances of the phrases such as "in one or more embodiments," "in certain embodiments," "in various embodiments," "in one embodiment" or "in an embodiment" in various places throughout this specification are not necessarily referring to the same embodiment. Furthermore, the particular features, structures, materials, or characteristics may be combined in any suitable manner in one or more embodiments.

Reference will now be made to figures wherein like structures will be provided with like reference designations. It is understood that the drawings are diagrammatic and schematic representations of exemplary embodiments, and are neither limiting nor necessarily drawn to scale.

The present disclosure relates to medical devices, systems and methods for enhancing visualization of an invasive procedure requiring procedural guidance, such as providing enhanced visualization of a vascular access device or wire device during an invasive insertion procedure. In one or more embodiments, a catheter assembly is provided which includes a catheter adapter subassembly and a wire subassembly. The catheter adapter subassembly includes either a permanent magnet element or magnetizable feature and the wire subassembly includes a permanent magnet element or a magnetizable feature. Thus, in one embodiment, the catheter adapter subassembly includes a permanent magnet and the wire subassembly includes a magnetizable feature. In another embodiment, the catheter adapter subassembly includes a magnetizable feature and the wire subassembly includes a permanent magnet. In other embodiments, a needle subassembly and a wire subassembly are provided. The needle subassembly includes either a permanent magnet element or magnetizable feature and the wire subassembly includes a permanent magnet element or a magnetizable feature. Thus, in one embodiment, the needle subassembly includes a permanent magnet and the wire subassembly includes a magnetizable feature. In another embodiment, the needle subassembly includes a magnetizable feature and the wire subassembly includes a permanent magnet. In another embodiment, the catheter adapter subassembly includes a magnetizable feature and the wire subassembly includes a permanent magnet. In other embodiments, a guidewire introducer subassembly and a wire are provided. The guidewire introducer subassembly includes either a permanent magnet element or magnetizable feature and the guidewire includes a permanent magnet element or a magnetizable feature. Thus, in one embodiment, The guidewire introducer subassembly includes a permanent magnet and the guidewire includes a magnetizable feature. In another embodiment, the guidewire introducer subassembly includes a magnetizable feature and the guidewire includes a permanent magnet.

For clarity it is to be understood that the word "proximal" refers to a direction relatively closer to a clinician using the device to be described herein, while the word "distal" refers to a direction relatively further from the clinician. For example, the end of a needle or wire placed within the body of a patient is considered a distal end of the needle or wire, while the needle or wire end remaining outside the body is a proximal end of the needle. "Magnetic feature" refers to a feature that includes a permanent magnet and/or a magnetizable material that has been magnetized by an externally applied magnetic field such that the magnetic feature can be detected by an ultrasound system. A "magnetizable feature" refers to an element that can become magnetized and is detectable by an ultrasound system as described further herein.

Figure 2:
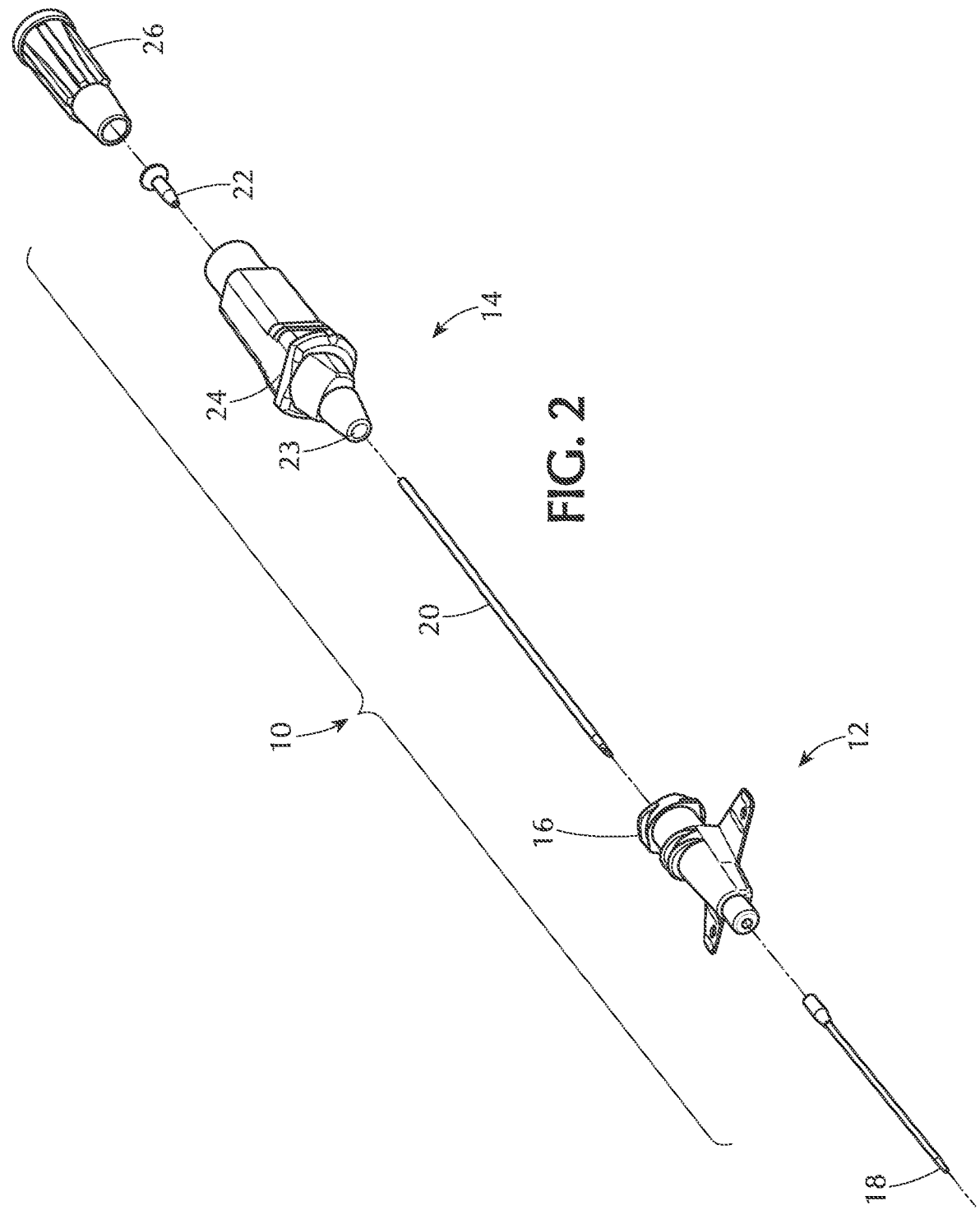
FIG. 2 is an exploded perspective view of the catheter assembly shown in FIG. 1.
Figure 3:
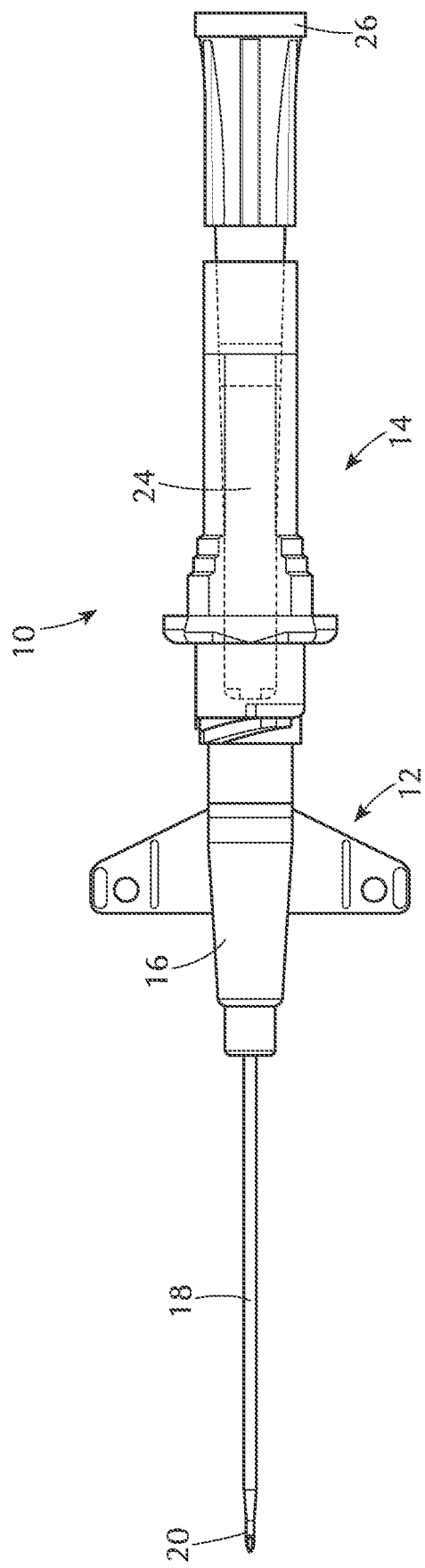
FIG. 3 is a top plan view of the catheter assembly shown in FIG. 1.

Referring now to FIGS. 1-3, an exemplary embodiment of a catheter assembly 10 is shown, including a catheter adapter subassembly 12 and a needle subassembly 14. The catheter adapter subassembly 12 comprises a catheter adapter 16, catheter tubing 18 and a securement element 22, and the needle subassembly 14 further includes a needle 20, connected to a needle hub, at a hub distal end 23 and a vent plug 26. In other embodiments not shown, the needle 20 can be retracted into the needle hub after the needle 20 has been used to prevent accidental needle sticks of a patient or a clinician.

Figure 4:
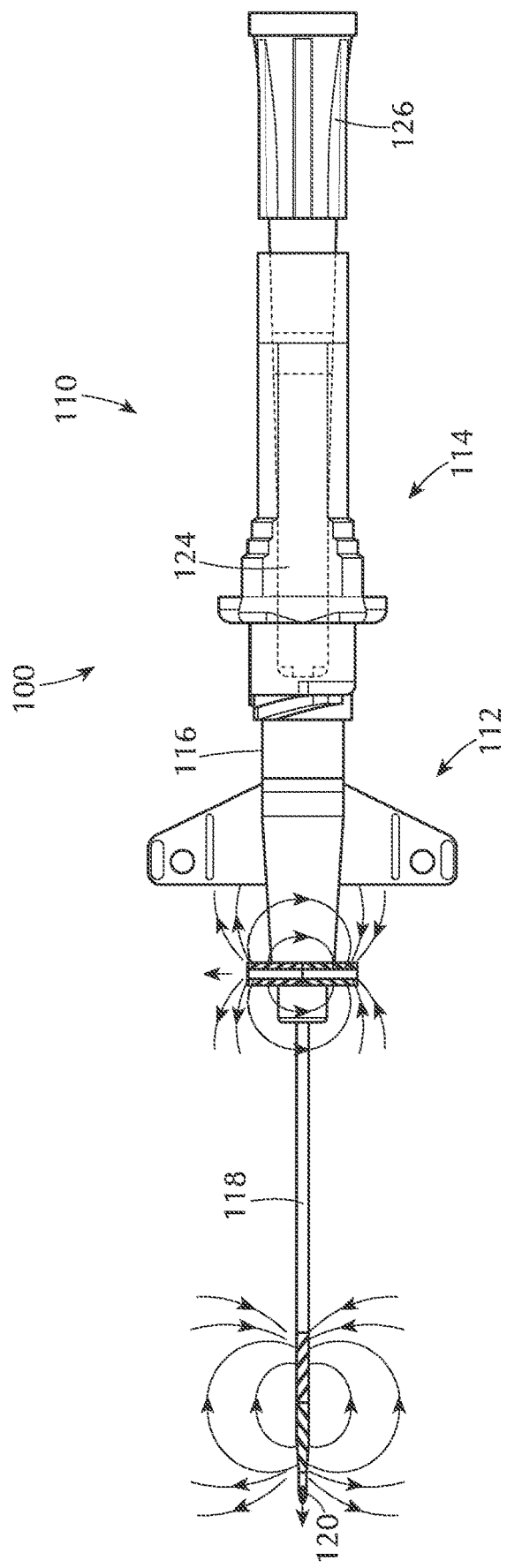
FIG. 4 is a top plan view of a catheter assembly according to an embodiment.

Referring now to FIGS. 4 and 5, an embodiment of a medical device 100 comprising a catheter assembly 110 is shown. The catheter assembly 110 includes a catheter adapter subassembly 112 and a needle subassembly 114. The catheter adapter subassembly 112 further includes a catheter adapter 116, catheter hub (not shown) and catheter tubing 118. The needle subassembly 114 further includes a needle 120, connected to a needle hub (not shown), disposed within a needle hub 124 and a vent plug 126. In the embodiment shown in FIGS. 4 and 5, the catheter adapter subassembly 112 includes a permanent magnet element 132 and the needle subassembly 114 includes a magnetizable feature 130, in particular on the needle 120. According to an alternative embodiment (not shown), this configuration is reversed wherein the permanent magnet element 132 is on the needle subassembly 114, in particular on the needle 120, and the magnetizable feature 130 is on the catheter adapter subassembly 112.

The use of a permanent magnet element on the catheter adapter subassembly 112 and a magnetizable feature on the needle subassembly 114 provides the ability to calculate the catheter tip position and the needle tip position based on known geometry relative to the position of permanent magnet element 132 on the catheter adapter subassembly 112 from which a calculated catheter tip position and a calculated needle tip position can be determined. The permanent magnet element 132 provides a static magnetic field, while the magnetizable feature 130 on the needle 120 can be magnetized with an externally applied magnetic field prior to insertion of the needle 120 into the patient.

In the embodiment shown in FIGS. 4 and 5, the magnetizable feature 130 is on the needle 120, and the catheter adapter subassembly 112 includes the permanent magnet element 132. The magnetizable feature 130 on the needle 120 can be provided in a variety of ways. In one embodiment, the needle 120 is made from a magnetizable material, for example, a steel material that has a magnetic permeability that permits the needle 120 to be magnetized by application of an external magnetic field. Stainless steel that is typically used to manufacture hypodermic needles for medical use, for example, type 304 stainless steel, may not have the magnetic permeability to be magnetized and used in a device according one or more embodiments. Type 304 stainless steel is an austenitic steel comprising at least 18% chromium, 8% nickel, and a maximum of 0.08% carbon. Type 316 stainless steel is also used in the manufacture of hypodermic needles, and type 316 stainless steel is also austenitic and non-magnetic. The nickel content of type 316 stainless steel is typically higher than type 304 stainless steel, and type 316 stainless steel also includes the addition of molybdenum. According to one or more embodiments, the needle 120 is made from martensitic or ferritic stainless steels, for example, type 420 or type 430 stainless steel.

In one or more embodiments, the magnetizable feature 130 on the needle comprises a separate feature on the needle 120. Referring now to FIG. 6A, in one embodiment, needle adhesive 140 is placed on a proximal end 121 of the needle 120, which can be used to secure the needle 120 to the hub within the needle chamber 24. The needle adhesive 140 can be any suitable adhesive such as a curable glue containing magnetizable nanoparticles such as magnetizable metal nanoparticles or magnetizable metal oxide nanoparticles. The magnetizable metal can include iron, cobalt, nickel and alloys of iron, cobalt, and nickel. According to one or more embodiments, the size of the magnetic nanoparticles is in the range of about 1 nanometer (nm) to about 100 nm. In one embodiment, adhesive is a light-curable glue, and in another embodiment, the adhesive is a heat-curable glue.

Referring now to FIG. 6B, an embodiment is shown in which the magnetizable feature is a needle ferrule 142 adjacent the distal tip 123 of the needle 120. The needle ferrule 142 is made from a magnetizable metal such as martensitic or ferritic stainless steels, for example, type 420 or type 430 stainless steel. The needle ferrule 142 provides at least a localized area of increased outer diameter. As used herein, the term "ferrule" refers to a separate member attached to the shank portion the needle 120, providing at least a localized area of increased outer diameter. The term "ferrule" includes a construction wherein the ferrule comprises an integral part of the needle, defining a one-piece monolithic construction composed of both the needle 120 and the needle ferrule 142, as well as a construction in which the needle ferrule 142 is a piece added to the needle by crimping the needle ferrule 142 onto the shank of the needle 120.

Referring now to FIG. 6C, an embodiment is shown in which the magnetizable feature is a spot weld 144 adjacent the distal tip 123 of the needle 120. The spot weld 144 can be made from a magnetizable metal such as martensitic or ferritic stainless steels, for example, type 420 or type 430 stainless steel.

Referring now to FIG. 6D, an embodiment is shown in which the magnetizable feature is a needle safety element, for example, a metal clip 146, specifically, a metal cannula safety clip adjacent the distal tip 123 of the needle 120. The metal clip 146 can be made from a magnetizable metal such as martensitic or ferritic stainless steels, for example, type 420 or type 430 stainless steel. In other embodiments, the needle safety element can be embodied in other forms, for example, a spring, a plastic housing including a magnetizable feature, or other suitable safety elements. According to one or more embodiments, the safety element can be made from a materials that are not magnetic or magnetizable and include a magnetizable or magnetic material.

Referring now to FIG. 6E, an embodiment is shown in which the magnetizable feature is a notch 148 in the needle 120, adjacent the distal tip 123 of the needle 120. The notch 148 can include an insert made from a magnetizable metal such as martensitic or ferritic stainless steels, for example, type 420 or type 430 stainless steel. The insert fits inside the notch 148 to completely or partially fill the notch 148. According to one or more embodiments, the insert can be a permanent magnet, magnetic adhesive or other magnetic material. The notch can be partially filled to occupy one-half the length of the notch 148.

Figure 7:
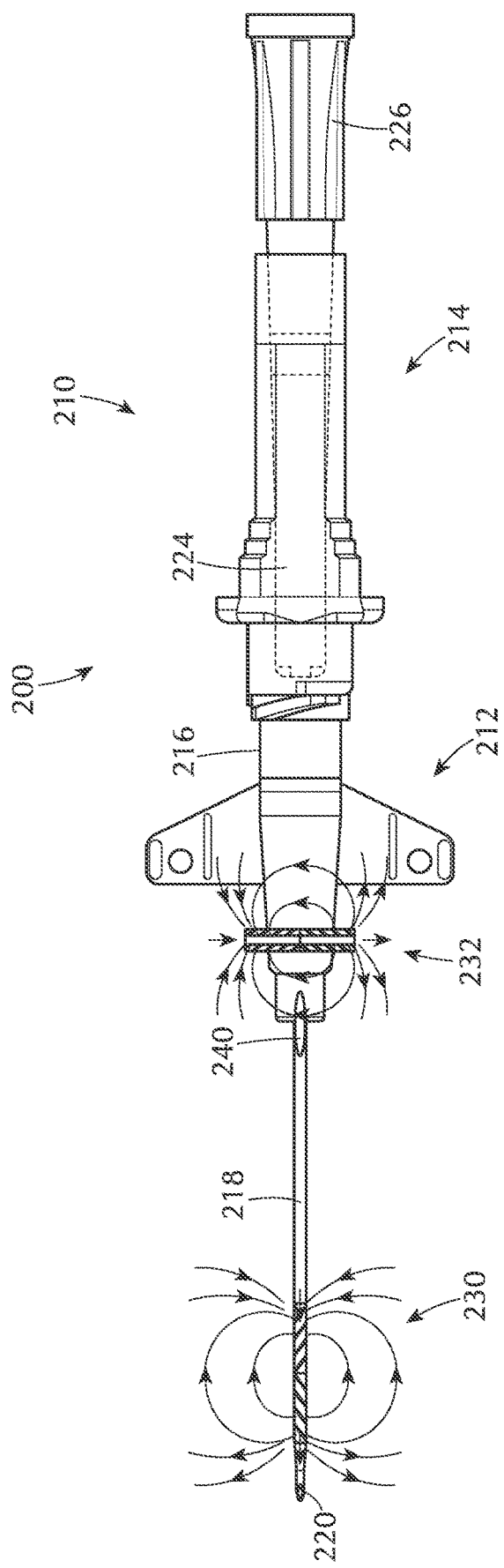
FIG. 7 is a top plan view of an embodiment of a catheter assembly according to an embodiment.

Referring now to FIG. 7, an embodiment of a medical device 200 comprising a catheter assembly 210 is shown. The catheter assembly 210 includes a catheter adapter subassembly 212 and a needle subassembly 214. The catheter adapter subassembly 212 includes a catheter adapter 216, catheter hub (not shown) and catheter tubing 218, and the needle subassembly 214 further includes a needle 220 connected to the needle hub 224, disposed within a needle hub 224 and a vent plug 226. In the embodiment shown in FIG. 7, the catheter adapter subassembly 212 includes a permanent magnet element 232 and the needle subassembly 214 includes a magnetizable feature 230, in particular on the needle 220. In the specific embodiment shown, the catheter adapter subassembly 212 includes the catheter tubing 218 and a catheter adapter 216, and a magnetic adhesive 240 attaches the catheter tubing 218 to the catheter adapter 216. The magnetic adhesive 240 can be any suitable adhesive such as a curable glue containing magnetizable nanoparticles such as magnetizable metal nanoparticles or magnetizable metal oxide nanoparticles. The magnetizable metal can include iron, cobalt, nickel and alloys of iron, cobalt, and nickel. According to one or more embodiments, the size of the magnetic nanoparticles is in the range of about 1 nanometer (nm) to about 100 nm. In one embodiment, adhesive is a light-curable glue, and in another embodiment, the adhesive is a heat-curable glue.

Figure 8:
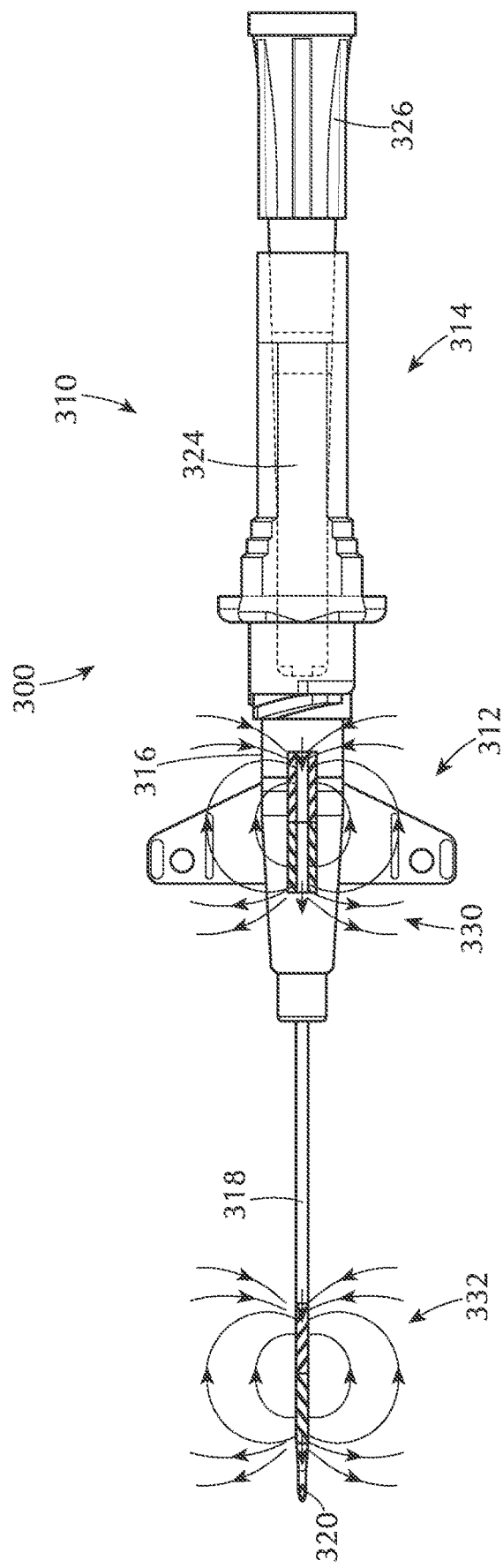
FIG. 8 is a top plan view of an embodiment of a catheter assembly according to an embodiment.
Figure 9:
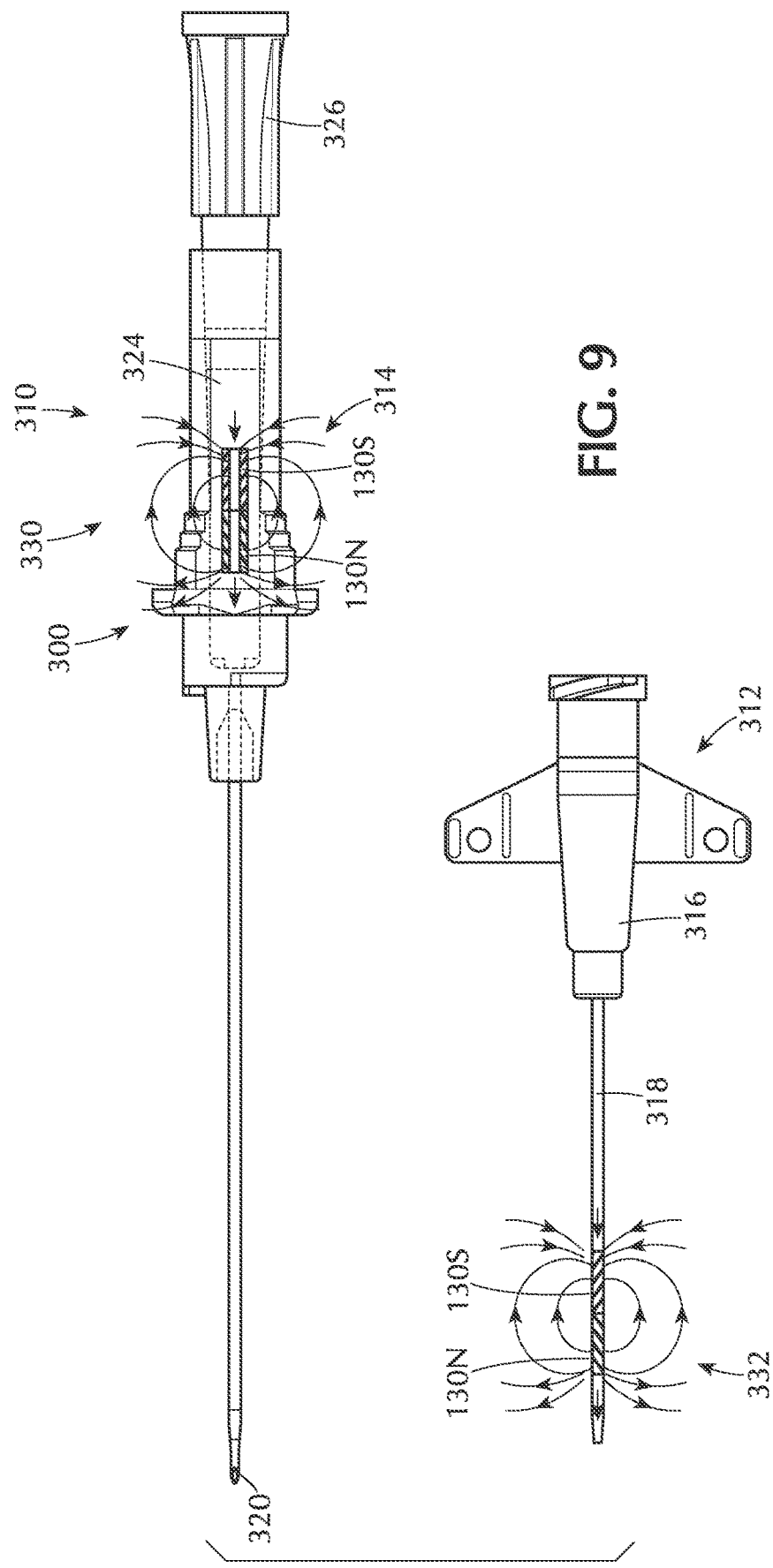
FIG. 9 shows the catheter assembly of FIG. 8 with the needle subassembly and catheter adapter subassembly separated.

Referring now to FIGS. 8 and 9, an embodiment of a medical device 300 comprising a catheter assembly 310 is shown. The catheter assembly 310 includes a catheter adapter subassembly 312 and a needle subassembly 314. The catheter adapter subassembly 312 includes a catheter adapter 316, catheter hub (not shown) and catheter tubing 318, and the needle subassembly 314 further includes a needle 320 connected to the needle chamber 324, disposed within a needle chamber 324 and a vent plug 326. In the embodiment shown in FIGS. 8 and 9, the catheter adapter subassembly 312 includes a magnetizable feature 330 and the needle subassembly 314 includes a permanent magnet element 332.

FIGS. 10A-10D show various configurations for providing the magnetizable feature 330 on the catheter adapter subassembly 312. In FIG. 10A, a securement element in the form of a mandrel 342, which can be a conical mandrel for connecting the catheter tubing 318 to the catheter adapter 316, can be the magnetizable feature. According to one or more embodiments, the mandrel 342 is includes or is manufactured from martensitic or ferritic stainless steels, for example, type 420 or type 430 stainless steel. It will be understood that in FIG. 10A, the mandrel 342 is protruding from the catheter adapter 316. In other embodiments (not shown), the mandrel 342 can be recessed within the catheter adapter 316.

In FIG. 10B, the securement element is shown in the form of a catheter tubing adhesive 340 is shown on the catheter tubing 318, which can be used to provide the magnetizable feature. The catheter tubing adhesive 340 can be any suitable adhesive such as a curable glue containing magnetizable nanoparticles such as magnetizable metal nanoparticles or magnetizable metal oxide nanoparticles. The magnetizable metal can include iron, cobalt, nickel and alloys of iron, cobalt, and nickel. According to one or more embodiments, the size of the magnetic nanoparticles is in the range of about 1 nanometer (nm) to about 100 nm. In one embodiment, adhesive is a light-curable glue, and in another embodiment, the adhesive is a heat-curable glue.

FIG. 10C shows an embodiment in which a blood control component 346 shown exploded from the catheter adapter subassembly 312 to provide the magnetizable feature. In the embodiment shown, the blood control component is a spring that includes a magnetic element or magnetizable material. According to one or more embodiments, the blood control component 346 includes martensitic or ferritic stainless steels, for example, type 420 or type 430 stainless steel. The blood control component (metal spring for instance) moves with the catheter adapter until fully advanced. It will be appreciated that in use the blood control component 346 in the form of a spring would be located within the catheter adapter 316, and may not be visible, unless the catheter adapter was made from transparent material.

FIG. 10D shows an embodiment in which a magnetic element 348 on the catheter adapter 316 provides the magnetizable feature. According to one or more embodiments, the magnetic element 348 is includes or is made from martensitic or ferritic stainless steels, for example, type 420 or type 430 stainless steel. A magnetic wedge can provide a controlled position on the catheter adapter subassembly 312 to provide a fixed measurement datum in a fixed location relative to the catheter distal tip and a wedge having a highly oriented grain structure due to the cold forming used during is fabrication is also beneficial in providing a measurement datum. In one or more embodiments, the various alternatives discussed with respect to FIGS. 10A-10D may not have a position that is as precisely controlled. In one or more embodiments, the wedge, spring, and safety clip, would rely on catheter tip calculated projection rather than positional measurement.

In specific embodiments that include a magnetic adhesive, the adhesive can include an additive selected from a paramagnetic additive, a ferromagnetic additive and combinations thereof. The additive, according to one or more embodiments, includes a component selected from powdered iron, magnetic iron oxide, magnetic titanium oxide, magnetic powdered steel, and a magnetic iron alloy, and mixtures thereof. In specific embodiments, the magnetic iron alloy includes one or more of nickel, zinc, and copper. In specific embodiments, the additive further comprises a component selected from chromium, magnesium, molybdenum and combinations thereof.

In one or more embodiments, the needle subassembly includes the permanent magnet element, and the catheter adapter subassembly includes the magnetizable feature, wherein the magnetizable feature includes magnetizable catheter tubing. In one or more embodiments, at least a portion of the polyurethane tubing comprises a magnetizable composition which is magnetizable by an externally applied magnetic field, the magnetizable composition comprising a magnetic material dispersed in the polyurethane. In certain embodiments, the magnetic composition is dispersed in the polymeric material, for example, polyurethane, which forms the tubing. In a specific embodiment, the magnetizable composition comprises an inner layer surrounding the lumen of the catheter with an outer layer of non-magnetizable polymeric material, for example, polyurethane. In an alternative specific embodiment, the layer of magnetizable composition is an outer layer surrounding an inner layer of non-magnetizable polyurethane. In one or more embodiments, the magnetizable composition forms longitudinal segments of the catheter separated by longitudinal segments of non-magnetizable polymeric material, for example, polyurethane.

In any of the foregoing embodiments of the catheter, the magnetizable composition may further comprise a radiopaque component. Alternatively, in any of the foregoing embodiments, a non-magnetizable portion of catheter may comprise a radiopaque component It will be understood that the permanent magnet element or a magnetized magnetizable feature for the embodiments described above, the orientation of the magnetic field can vary. The permanent magnet element can have north and south poles on axis with the catheter tubing and with the needle. Alternatively, permanent magnet element or magnetized magnetizable feature can have north and south poles off axis with the catheter tubing and with the needle, for example, the north and south poles can be oriented perpendicular to the longitudinal axis of the catheter tubing and the needle. For example, in FIG. 5, the magnetizable feature 130 is shown as being magnetized with the north pole 130N and south pole 130S of the magnetizable feature 130 oriented parallel of the longitudinal axis of the needle 120. The permanent magnet element 132 associated with the catheter adapter subassembly 112 is shown with the north pole 132N and south pole 132S oriented perpendicular to the longitudinal axis of the catheter tubing 118. In the configuration shown in FIG. 9, the permanent magnet element 332 and the magnetizable feature 330, which has been magnetized, are shown with the poles 330N, 330S, 332N and 332S oriented parallel to the longitudinal axis of the needle 320 and the catheter tubing 318. Other variants are possible such as the permanent magnet element and the magnetizable feature which has been magnetized having their north and south poles both oriented perpendicular or orthogonal to the longitudinal axis of the needle and the catheter tubing.

Figure 11:
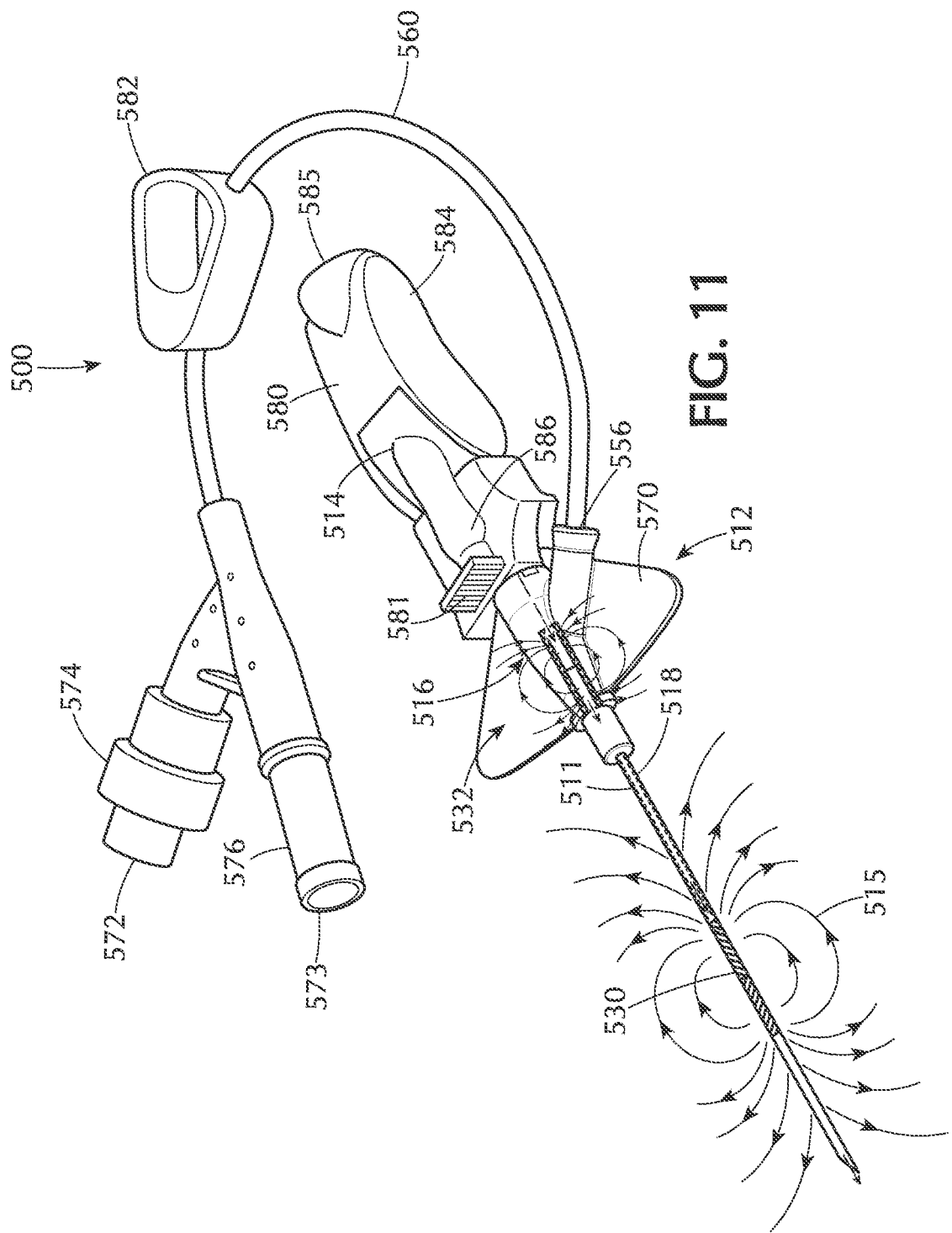
FIG. 11 is a perspective view of a catheter assembly showing optional features.

An example of a vascular access device including a catheter according to any of the foregoing embodiments described above is illustrated in FIG. 11. The vascular access device 500 shown in FIG. 11 comprises a catheter adapter subassembly 512 including a catheter adapter body 516 and a catheter tubing 518 and a permanent magnet element 532. A needle (not shown) within the catheter tubing includes magnetizable feature 530, which has been magnetized by application of an external magnetic field and can be any of the magnetizable features described herein. Magnetizing the magnetizable feature 530 with an externally applied magnetic field creates a magnetic field 515 in the region of magnetizable feature 530.

The vascular access device 500 may include a lateral access port 556 and may be connected to a section of an extension tube 560 for establishing fluid communication between an IV fluid source and the catheter tubing 518. In one or more embodiments, the extension tube 560 is built-in to reduce contamination and mechanical phlebitis by eliminating manipulation at the insertion site. In one or more embodiments, the extension tube 560 is compatible with high pressure injection. In one or more embodiments, the extension tube 560 provides continuous confirmation of vessel access during advancement of the catheter into the patient vein.

In one or more embodiments, a needle 511 of a needle subassembly 514 is inserted into the lumen (not show) of the catheter tubing 518. The needle subassembly 514 is shown as including finger grips 584 positioned at the sides of the needle subassembly 514 to facilitate various insertion techniques. In one or more embodiments, bumps may be present on the finger grip to indicate where to the user may grip the device for needle removal. In one or more embodiments, a thumb pad 585, having a gently convex surface, is provided at the proximal end of the needle subassembly 514. A flange 586, having a gently convex surface, is provided at the proximal end of the needle subassembly 514 to provide a finger pad. A wing member 570, thumb pad 585 and flange 586 may be utilized by the user during insertion, permitting the user to elect which insertion technique to employ.

In one or more embodiments, the needle subassembly 514 includes a needle shield 580. The needle shield 580 may be a design adapted to secure the tip of the needle within the shield after use. In one or more embodiments, the needle shield 580 may be activated passively. The needle tip is completely covered by the needle shield 580 in a fixed position. In one or more embodiments, a ferrule, crimp or other structure may be included near the tip for engagement with a needle shield in certain applications.

A push tab 581 may be provided to facilitate catheter advancement during insertion. The push tab 581 also allows for one-handed or two-handed advancement. In one or more embodiments, the push tab 581 is removed with the needle shield 580. A clamp 582 may also be included on the extension tubing to prevent blood flow when replacing the access port.

In one or more embodiments, the vascular access device 500 further includes a first luer access 572 and a second luer access 573 in fluid communication with the extension tube 560, a blood control split septum 574 associated with the first luer access 572, and an air vent 576 associated with the second luer access 573. Split septum 574 allows for a reduction in catheter-related bloodstream infection (CRBSI) while providing unrestricted flow and a straight fluid path and functions as a blood control septum. In one or more embodiments, the split septum 574 may be located in an internal cavity of the catheter adapter or on the distal end of the catheter adapter. In yet another embodiment, the split septum 574 may be located on a distal end of the extension tube 560. The air vent 576 allows air to escape from the system during insertion, providing continuous confirmation of vascular access while preventing leakage of blood from the system during insertion. In one or more embodiments, the air vent 576 may be at the distal end of extension tube 560.

Another aspect of the disclosure pertains to a system for determining catheter tip location when the catheter tubing is inserted in a patient. According to one or more embodiments, a system provides a way to independently measure the cannula tubing tip location by measuring the location and vector of the permanent magnet, and calculating and predicting the catheter tip location relative to the position of the magnetic sensor(s) on an ultrasound probe and the ultrasound information transmitted from the sensors on the ultrasound probe. A permanent magnet on a device with north and south poles on axis with the catheter and needle and a known geometrical relationship to one or more features fixed on the catheter assembly provides a measurement datum that is measureable by the ultrasound probe magnetic sensors. From the measurement datum based on the one or more features on the catheter assembly, the direction vector and position of the catheter tip, needle tip or other features can be calculated. A magnetized magnetizable needle or feature on the needle can then be used to independently measure the position feature and calculate the position of the needle tip. The calculated position of the needle tip or feature on the needle can then be compared relative to the calculated position of the catheter tip to provide more specific information related to the catheter placement process, such as needle and catheter tip position relative to the patient's anatomy. This information can be used to determine (a) if the catheter is properly seated and ready for insertion (i.e., no over the bevel condition), (b) when the needle tip is in the "hooded" position (needle tip just inside of the catheter tip), and (c) and (d) when the catheter is advanced to specific distances and at angles suggesting successful placement in the vein.

Referring now to FIGS. 12A-D, an embodiment of a medical device 600 comprising a catheter assembly 610 is shown. The catheter assembly 610 includes a catheter adapter subassembly 612 and a needle subassembly 614. The catheter adapter subassembly 612 includes a catheter adapter 616, catheter hub (not shown) and catheter tubing 618 having a distal catheter tip, and the needle subassembly 614 further includes a needle 620 having a needle distal tip 623 connected to a needle hub 624, and a vent plug 626. In the embodiment shown in FIGS. 12A-D, the catheter adapter subassembly 612 includes a permanent magnet element 632 and the needle subassembly 614 includes a magnetizable feature 630. FIG. 12B shows the catheter assembly 610 in 12A in when the needle distal tip 623 is in the "hooded" position where the needle distal tip 623 is just inside of the catheter distal tip 619. Since the dimensions of the components of the needle subassembly 614 are fixed and known, placement of the permanent magnet element 632 provides a known geometrical relationship, for example, distance and angular position, with respect to one or more features fixed on the catheter assembly, which provides a measurement datum 633.

Referring now to FIG. 12C, the catheter adapter subassembly 612 has been advanced in distal direction (toward the patient and away from the clinician), and the measurement datum 633 can be used to determine the distance and angular movement of the needle 620 with respect to the measurement datum 633. Similarly, if the catheter tubing 618 or other part of the catheter adapter subassembly 612 includes a magnetizable feature, and the needle subassembly 614 includes a permanent magnet, the distance and the angular movement of the catheter tubing 618 can be determined with respect to the measurement datum. FIG. 12C shows that the needle 620 has moved a distance D1, and the magnetizable feature 630 has moved a distance D1 from the catheter distal tip 619. In FIG. 12D, the needle subassembly 614 has moved in a proximal direction (towards the clinician) for a distance D2, and the magnetizable feature 630 is now at a distance D2 from the catheter distal tip 619. Each sequential movement of either a permanent magnet element or magnetized magnetizable feature on a needle and/or the cannula can be measured and tracked using an ultrasound system.

Figure 13:
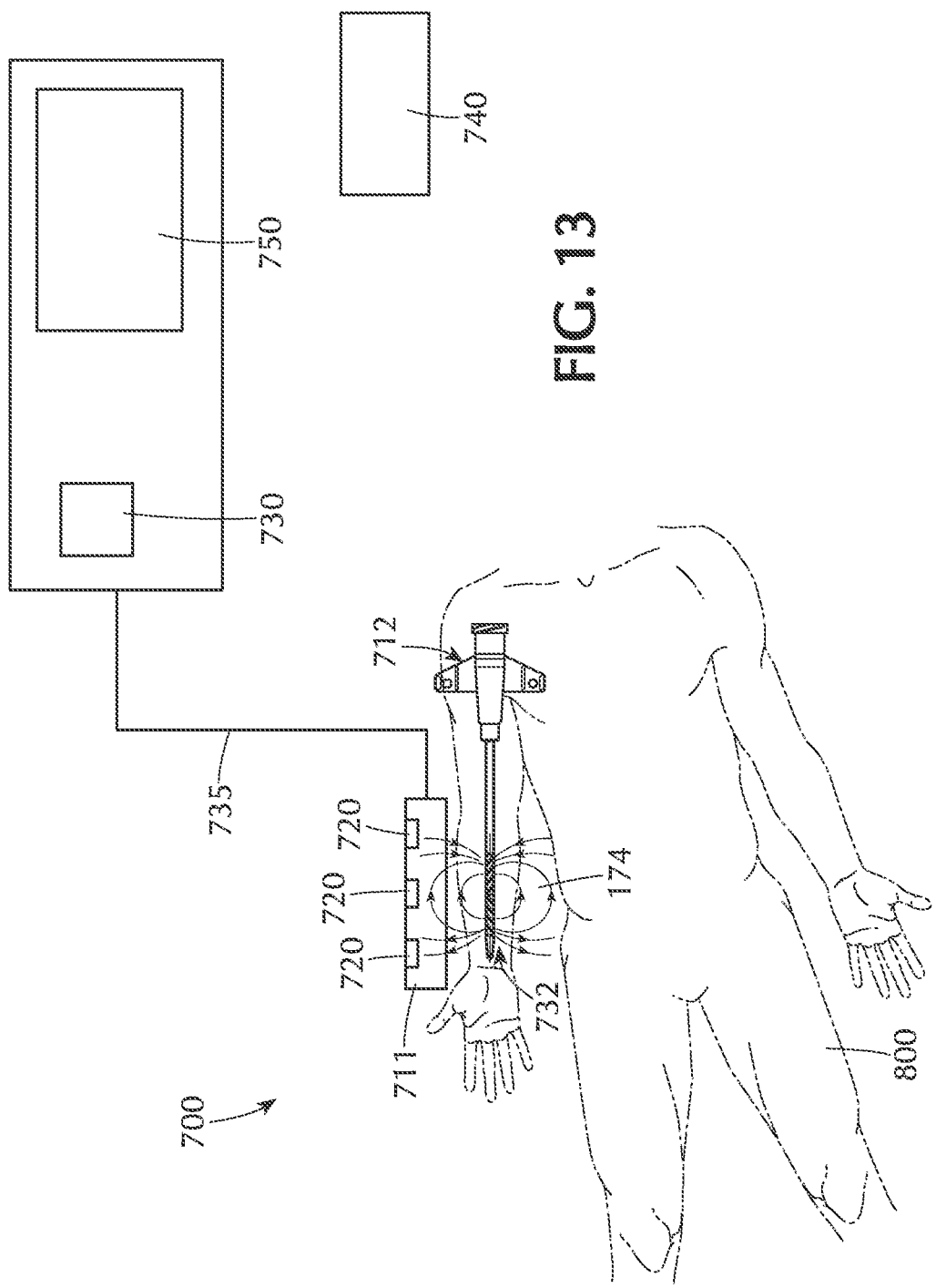
FIG. 13 shows an embodiment of a system.

The location of the magnetized magnetic feature or permanent magnet on a needle or cannula tubing can be accomplished by using a magnetometer to determine the strength of the magnetic field and its direction. As used herein, "magnetometer" refers to a device that detects a magnetic field. In specific embodiments, magnetometers may measure the strength of a magnetic field. When invasive needle or catheter is magnetic and produces a known magnetic field B at a given distance x through tissue of permeability $\mu_r$, a mathematical correlation between the two i.e. $x=f(B, \mu_r)$ can be derived. In an embodiment, three different magnetometers are arranged in a three-dimensional grid array, orthogonal to each other, are used, and a three-dimensional (3D) correlation can be derived where $I=f(B_i, \mu_r)$, where i=x or y or z along three axes. Such correlation can be extended to an array of 3-dimensional (3-D) magnetometers to obtain the precise distance to the magnetized catheter or vascular access device from the array of 3D magnetometers. If the location of the array of 3D magnetometers is known in reference to the ultrasound sensor, then the precise location of the magnetized device with respect to the ultrasound sensor can be calculated. An inferred image of the device can then be created and superimposed over the ultrasound image and displayed. An exemplary magnetic sensing method using magnetometers and a lookup table instead of a mathematical function to determine the location of a magnetized invasive device from the magnetic field strength measured outside the body using magnetometers is shown and described in United States Patent Application Publication Number US20140257080 A1. The method described in US20140257080 A1 can be adapted as described herein, for example, a three-dimensional (3D) correlation is from a mathematical function, and the correlation is extended to an array of 3-dimensional (3-D) magnetometers, one of the magnetometers outside the patient's body, to obtain the precise distance to the magnetized catheter or vascular access device from the array of 3D magnetometers. Another exemplary method of referencing the magnetometers with respect to an ultrasound probe is described in PCT Patent Application Publication Number WO2013034175 A1, which can be adapted as described herein. For example, as shown in FIG. 13, an ultrasound system 700 is shown including a catheter adapter subassembly 712 comprising a magnetizable feature 732 that has been magnetized as described herein is shown inside of a patient's body 800. It will be appreciated that the sizes shown are not to proportion and the sizes of the catheter adapter subassembly 712 and the magnetizable feature 732 are exaggerated in size to illustrate these elements more clearly. A magnetometric detector 711 comprising an array of magnetometers 720 (which can be housed in a probe of a ultrasound system, not shown) arranged in a 3-D array can be used to sense the magnetic field 714 together with the terrestrial magnetic field and any other background magnetic field. The magnetometric detector 711 is in communication with an ultrasound processor 730 adapted to determine from the detected field the position and orientation of the magnetizable feature 732 relative to the magnetometric detector

711. This magnetically detected position is then displayed on a display 750 together with the ultrasound image.

The ultrasound system 700 can be a standard two dimensional B-mode ultrasound system with a standard ultrasound probe modified by the provision of the magnetometric detector 711. The ultrasound processor 730, which can be connected to the ultrasound probe via a cable 735, sends electrical signals to the magnetometric detector 711 to cause it to generate ultrasound pulses and interpreting the raw data received from the transducer probe housing the magnetometric detector 711, which represents echoes from the patient's body, to assemble it into an image of the patient's tissue.

The magnetometric detector 711 can be attached to the ultrasound probe and can be battery powered or powered from the ultrasound system. In specific embodiments, positioning elements are provided on the magnetometric detector 711 to ensure that it is always attached in the same well-defined position and orientation. The magnetometric detector 711 can connected by a wireless connection to a base unit 740 which is in wireless or wired (e.g. USB) communication with the ultrasound processor 730 and the display 750. The base unit 740 can be integrated with, or some of its functions performed by, the ultrasound processor 730 or the magnetometric detector 711.

The base unit 740 receives normalized measurements from magnetometric detector 711 and calculates the position, or optionally the position and orientation, of magnetizable feature 732. The base unit 740 can also receive additional information such as the state of charge of the magnetometric detector's battery and information can be sent from the base unit 740 to the magnetometric detector 711, such as configuration information. The base unit 740 forwards the results of its calculations, i.e. the position and, optionally, orientation, to the ultrasound processor 730 for inclusion in the displayed ultrasound image of an image of the catheter.

In one or more embodiments, the base unit 740 can be integrated into the ultrasound system 700 with the ultrasound processor 730 and the magnetometric detector 711 being in direct communication with the ultrasound system 700 either via wireless link or using the same physical cable 735.

Thus, in one or more embodiments, the magnetizable feature is magnetized using any suitable device that can produce an magnetic field to magnetize a needle or medical device to produce a magnetic field B at a distance x through tissue of permeability $\mu_r$, and the correlation is calculated as $x=f(B, \mu_r)$. In one or more embodiments, three magnetometers 720 are placed orthogonally to each other are used to derive a 3-dimensional correlation $I=f(B_i, \mu_r)$, wherein $i=x$ or y or z along three axes. In a specific embodiment, the distance from the magnetizable feature to the 3-dimensional array of magnetometers is calculated. In a further specific embodiment, location of the array of magnetometers in reference to an ultrasound sensor of an ultrasound imaging system is used to calculate a location of the magnetizable feature with respect to the ultrasound sensor. In another specific embodiment, the method comprises displaying an image of the magnetizable feature.

As described above with respect to FIGS. 12A-D, providing a permanent magnet on the needle subassembly and a magnetizable feature on the catheter adapter subassembly (or a reverse configuration in which the magnetizable feature is on the needle subassembly (e.g., the needle or needle hub) and the permanent magnet is on the catheter adapter subassembly) relative positions of a catheter tip and a needle cannula tip can be determined by utilizing an ultrasound system including a three dimensional array of magnetometers. Relative positional changes of the catheter adapter subassembly and needle subassembly can be determined in three axes, x, y and z, as well relative changes in angular motion w of the catheter adapter subassembly and the needle subassembly based on based on a known geometrical relationship to one or more features fixed on the catheter adapter assembly or needle subassembly, which provides a measurement datum that is measureable by the ultrasound probe magnetic sensors. From the measurement datum based on the one or more features, the direction vector and position of the catheter tip or other features can be calculated based on a 3-dimensional correlation $I=f(B_i, \mu_r)$, wherein $i=x$ or y or z along three axes or predict relative motion between the needle hub and catheter adapter sub-assemblies. Understanding the relative position and motion of these two sub-assemblies can be used to inform a clinician of procedurally important states of the insertion process, such as when the needle tip reaches the vein, when the catheter tip reaches the vein, when the catheter is advanced to cover the needle tip ("hooding the catheter") and thereby safe for further advancement.

Another aspect of the disclosure comprises methods that can be practiced according to any of the previously described systems. A method for determining a relative position of a catheter tip and a needle cannula tip, the method includes providing a catheter having a catheter distal tip and a needle having a needle distal tip, associating a permanent magnet element with one of the catheter and the needle, associating a magnetizable feature with the other of the catheter and the needle, obtaining a measured position of the permanent magnet, obtaining a measured position of the magnetizable feature to obtain a calculated position of the catheter distal tip, and comparing the calculated position of the catheter distal tip with the calculated position of the needle distal tip to determine the relative position of the catheter distal tip and the needle distal tip. In one embodiment, the needle includes the magnetizable feature and the catheter includes the permanent magnet and the relative position of the catheter distal tip and the needle distal tip indicates that the catheter is properly seated on the needle. In another embodiment, the relative position of the catheter distal tip and the needle distal tip indicates that the catheter is in a hooded position on the needle. In another embodiment, the relative position of the catheter distal tip and the needle distal tip indicates that the catheter distal tip is advanced a specific distance or angle.

In one embodiment of the method, the catheter adapter subassembly includes the magnetizable feature and the needle subassembly includes the permanent magnet, and relative movement of the catheter adapter subassembly and needle subassembly is determined by a three-dimensional array of magnetometers positioned in proximity to at least one of the permanent magnet the magnetizable feature. In one embodiment of the method, the method includes magnetizing the magnetizable feature by applying an external magnetic field to the magnetizable feature. In one embodiment, the three-dimensional array of magnetometers is part of an ultrasound system, and the ultrasound system derives a three-dimensional correlation to obtain a distance from the grid array to the magnetizable feature or permanent magnet. In another embodiment, the three-dimensional correlation is determined by the function $I=f(B_i, \mu_r)$, where $i=x$ or y or z along three axes, x, y and z are distances in three planes, B is a known magnetic field produced by the permanent magnet or magnetizable feature, and $\mu_r$ is magnetic permeability.

In another embodiment of the method, the catheter adapter subassembly includes the permanent magnet and the needle subassembly includes the magnetizable feature, and relative movement of the catheter adapter subassembly and needle subassembly is determined by a three-dimensional array of magnetometers positioned in proximity to at least one of the permanent magnet the magnetizable feature. In one embodiment, the method includes magnetizing the magnetizable feature by applying an external magnetic field to the magnetizable feature. According to another embodiment, the three-dimensional array of magnetometers is part of an ultrasound system, and the ultrasound system derives a three-dimensional correlation to obtain a distance from the grid array to the magnetizable feature or permanent magnet. In one embodiment, the three-dimensional correlation is determined by the function $I=f(B_i, \mu_r)$, where i=x or y or z along three axes, x, y and z are distances in three planes, B is a known magnetic field produced by the permanent magnet or magnetizable feature, and $\mu_r$ is magnetic permeability.

Another aspect of the disclosure pertains to a catheter adapter subassembly comprising a magnetic feature selected from the group consisting of a metal mandrel for connecting catheter tubing to the hub, a catheter tubing adhesive, a blood control component of the catheter adapter subassembly, and a magnetic wedge on the catheter adapter body. The catheter adapter subassembly may further comprise magnetic catheter tubing. According to an embodiment, the metal mandrel comprises austenitic stainless steel.

Figure 14:
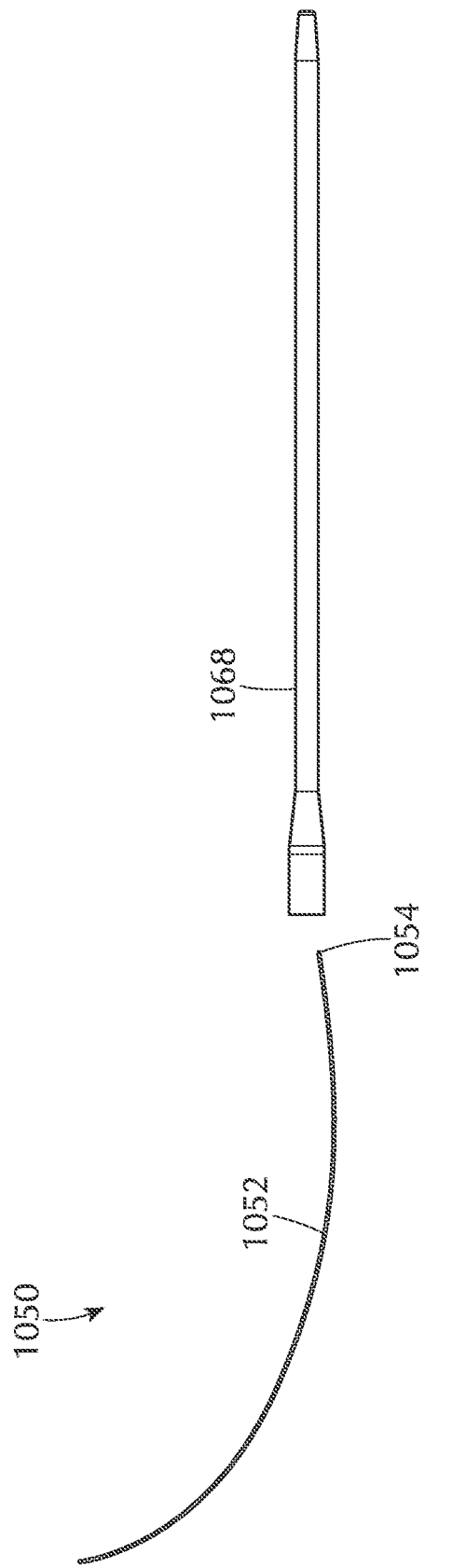
FIG. 14 shows an embodiment of a wire and a catheter.

While the embodiments of invasive medical devices described in this disclosure primarily are directed to needles, it will be understood that the invasive medical device can also be in the form of a wire, which may be in the form of a guidewire, a catheter introducer or a stylet. Thus, as used herein, "wire" refers to a medical wire that is configured and adapted to be used in a medical procedure by insertion into the body of a patient, for example, a patient's vasculature, or other part of the body such as a patient's pleural cavity or vertebral space. As used herein, "stylet" refers to a wire run through a catheter or cannula to render it stiff or to remove debris from its lumen. A "catheter introducer" refers to wire used to facilitate insertion of an intravenous catheter. A "guidewire" is a wire that can be used to guide a catheter into place during venous catheter and other bodily catheter insertions. In venous insertions, the purpose of a guidewire is to gain access to the blood vessels using a minimally invasive technique. FIG. 14 depicts a wire 1050, which may be in the form of a catheter introducer, stylet or guidewire, which is sized and shaped to be inserted into an intravenous catheter 1068. The guidewire, stylet or catheter introducer has an elongate shaft 1052 and a distal tip 1054 that can be inserted into the intravenous catheter 1068 or directly into a patient, such as in pleural placement technique to place a pleural catheter.

Other embodiments pertain to medical devices, systems and methods including a wire or wire subassembly in combination with a catheter adapter subassembly and/or needle subassembly. The wire or wire subassembly can include a permanent magnet, and the catheter adapter subassembly and/or needle subassembly can include the magnetizable feature. Alternatively, the wire or wire subassembly can include a magnetizable feature to provide a magnetizable wire, and the catheter adapter subassembly and/or needle subassembly can include the permanent magnet. In other embodiments, a guidewire introducer assembly includes a guidewire introducer subassembly and a guidewire, wherein one of the guidewire introducer subassembly includes a permanent magnet and the guidewire includes a magnetizable feature. In an alternative embodiment, the association of the permanent magnet and magnetizable feature with the guidewire and guidewire introducer subassembly can be reversed.

Figure 15:
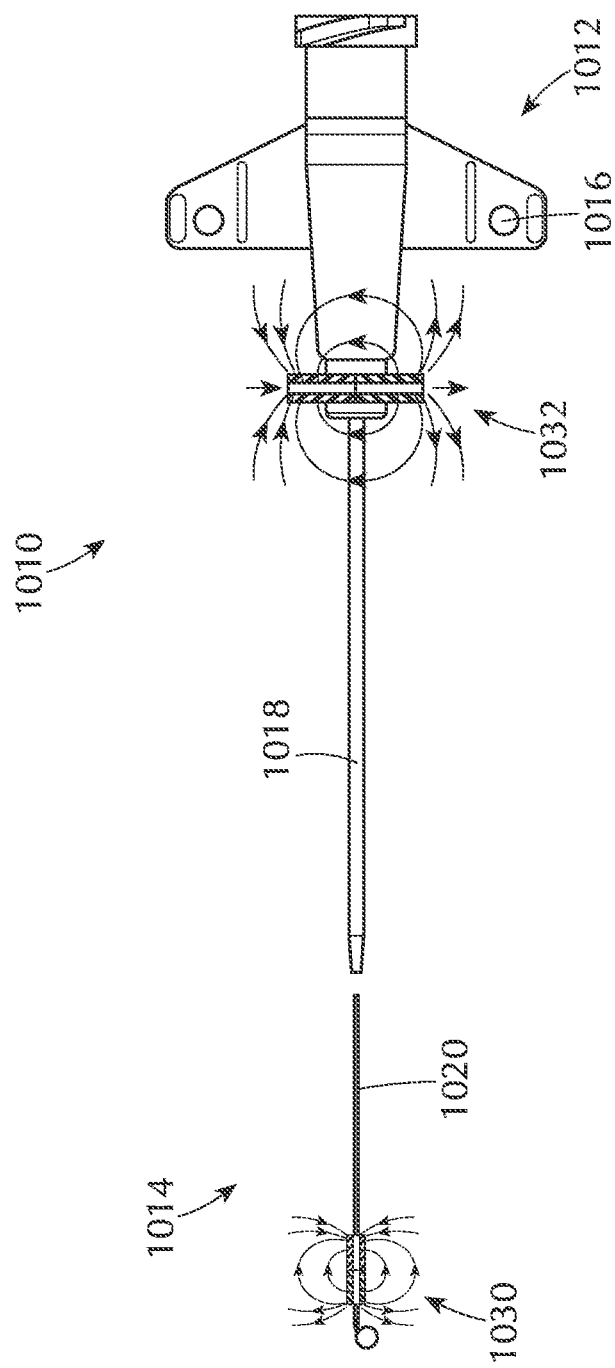
FIG. 15 shows an embodiment of a medical device including a catheter adapter subassembly and a wire subassembly.

Referring now to FIG. 15, an embodiment of a medical device comprising a catheter assembly 1010 is shown. The catheter assembly 1010 includes a catheter adapter subassembly 1012 and a wire assembly in the form of guidewire subassembly 1014. The wire assembly could also be in the form of a stylet or other medical wire. The catheter adapter subassembly 1012 further includes a catheter adapter 1016, catheter hub (not shown) and catheter tubing 1018. The guidewire subassembly 1014 further includes a guidewire 1020, which may be connected to an introducer body (not shown). In the embodiment shown in FIG. 15, the catheter adapter subassembly 1012 includes a permanent magnet element 1032 and the guidewire subassembly 1014 includes a magnetizable feature 1030, in particular on the guidewire 1020 to provide a magnetizable guidewire. According to an alternative embodiment (not shown), this configuration is reversed wherein the permanent magnet element 1032 is on the guidewire subassembly 1014, in particular on the guidewire 1020, and the magnetizable feature 1030 is on the catheter adapter subassembly 1012.

The use of a permanent magnet element on the catheter adapter subassembly 1012 and a magnetizable feature on the guidewire subassembly 1014 provides the ability to calculate the catheter tip position and the guidewire tip position based on known geometry relative to the position of permanent magnet element 1032 on the catheter adapter subassembly 1012 from which a calculated catheter tip position and a calculated guidewire tip position can be determined. The permanent magnet element 1032 provides a static magnetic field, while the magnetizable feature 1030 on the guidewire 1020 can be magnetized with an externally applied magnetic field prior to insertion of the guidewire 1020 into the patient.

In the embodiment shown in FIG. 15, the magnetizable feature 1030 is on the guidewire 1020, and the catheter adapter subassembly 1012 includes the permanent magnet element 1032. The magnetizable feature 1030 on the guidewire 1020 can be provided in a variety of ways. In one embodiment, the guidewire 1020 is made from a magnetizable material, for example, a steel material that has a magnetic permeability that permits the guidewire 1020 to be magnetized by application of an external magnetic field. Type 304 stainless steel may not have the magnetic permeability to be magnetized and used in a device according one or more embodiments. Type 304 stainless steel is an austenitic steel comprising at least 18% chromium, 8% nickel, and a maximum of 0.08% carbon. Type 316 stainless steel is also austenitic and non-magnetic. The nickel content of type 316 stainless steel is typically higher than type 304 stainless steel, and type 316 stainless steel also includes the addition of molybdenum. According to one or more embodiments, the guidewire 1020 is made from martensitic or ferritic stainless steels, for example, type 420 or type 430 stainless steel. Similar to the embodiments shown above with respect to FIGS. 6A-6E, the magnetizable feature of the wire subassembly can be one or more of an adhesive, the wire, a notch in the wire, a ferrule on the wire, and a spot weld on the wire. In embodiments in which the wire subassembly includes the magnetizable feature, and the catheter adapter subassembly includes a catheter adapter body, catheter tubing and the permanent magnet element, the permanent magnet element can be selected from the group consisting of a metal mandrel for connecting catheter tubing to the catheter adapter body, a catheter tubing adhesive, a blood control component of the catheter adapter subassembly, and a magnetic wedge on the catheter adapter body. In embodiments in which the wire subassembly includes the permanent magnet element, and the catheter adapter subassembly includes the magnetizable feature, the magnetizable feature can includes magnetizable catheter tubing.

Figure 16:
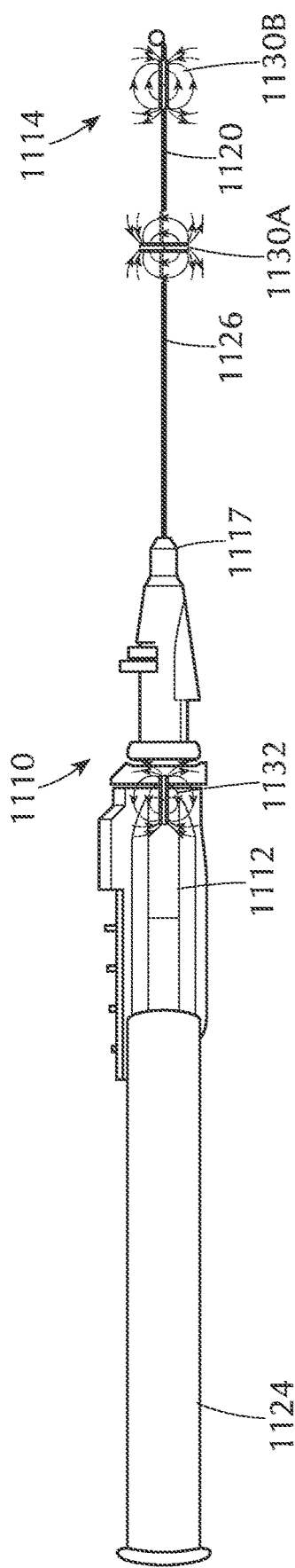
FIG. 16 shows an embodiment of a medical device including a needle subassembly and a wire subassembly.
Figure 17:
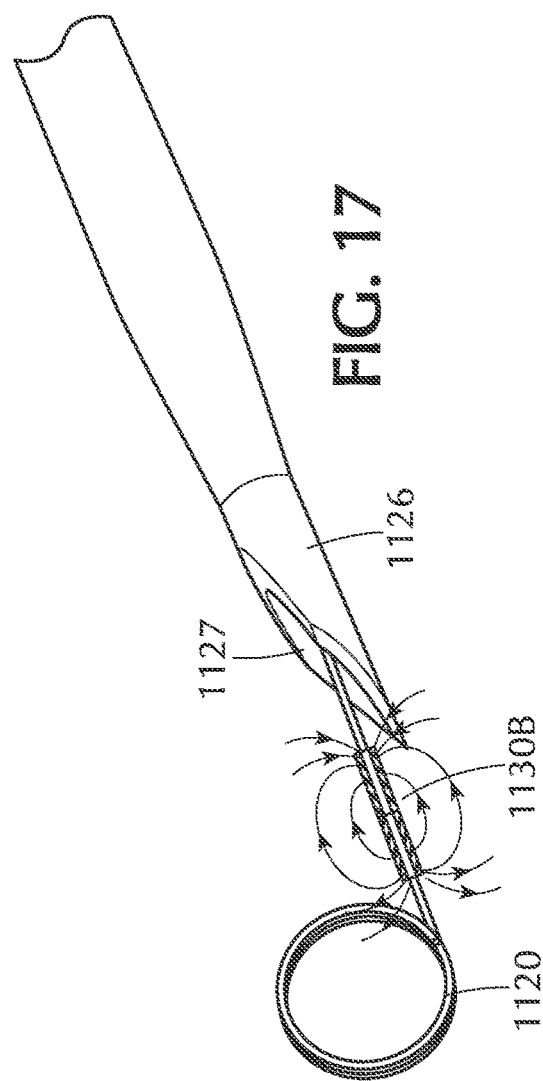
FIG. 17 shows a wire inserted through a needle lumen.

Referring now to FIGS. 16 and 17, an embodiment of a medical device 1110 including a needle subassembly 1112 and a guidewire subassembly 1114. The needle subassembly 1112 further includes needle hub 1117, a vent plug 1124 and a needle 1126. The guidewire subassembly 1114 further includes a guidewire 1120, which may be connected to an introducer body (not shown). In the embodiment shown in FIG. 15, the needle subassembly 1112 includes a permanent magnet element 1132 and the guidewire subassembly 1114 includes a magnetizable feature 1130A and a second magnetizable feature 1130B, in particular on the guidewire 1120. According to an alternative embodiment (not shown), this configuration is reversed wherein the permanent magnet element 1132 is on the guidewire subassembly 1114, in particular on the guidewire 1120, and the magnetizable feature 1130 is on the needle subassembly 1112.

The use of a permanent magnet element on the needle subassembly 1112 and a magnetizable feature on the guidewire subassembly 1114 provides the ability to calculate the needle tip position and the guidewire tip position based on known geometry relative to the position of permanent magnet element 1132 on needle subassembly 1112 from which a calculated needle tip position and a calculated guidewire tip position can be determined. The permanent magnet element 1132 provides a static magnetic field, while the magnetizable feature 1130 on the guidewire 1120 can be magnetized with an externally applied magnetic field prior to insertion of the guidewire 1120 into the patient. In embodiments in which the wire subassembly includes the magnetizable feature and the needle subassembly includes the permanent magnet element, and the magnetizable feature of the wire subassembly can be an adhesive, the needle, a ferrule on the wire, and a spot weld on the wire. In embodiments in which the needle subassembly includes the magnetizable feature and the wire subassembly includes the permanent magnet element, and the magnetizable feature of the needle subassembly can be a needle adhesive, the needle, a needle safety element, a notch, a needle ferrule, and a spot weld. As shown in FIG. 17, the needle subassembly further comprises a needle cannula having a hollow lumen 1127 and the guidewire 1120 is inserted through the lumen 1127, wherein the guidewire includes one of a permanent magnet element and a magnetizable feature.

Figure 18:
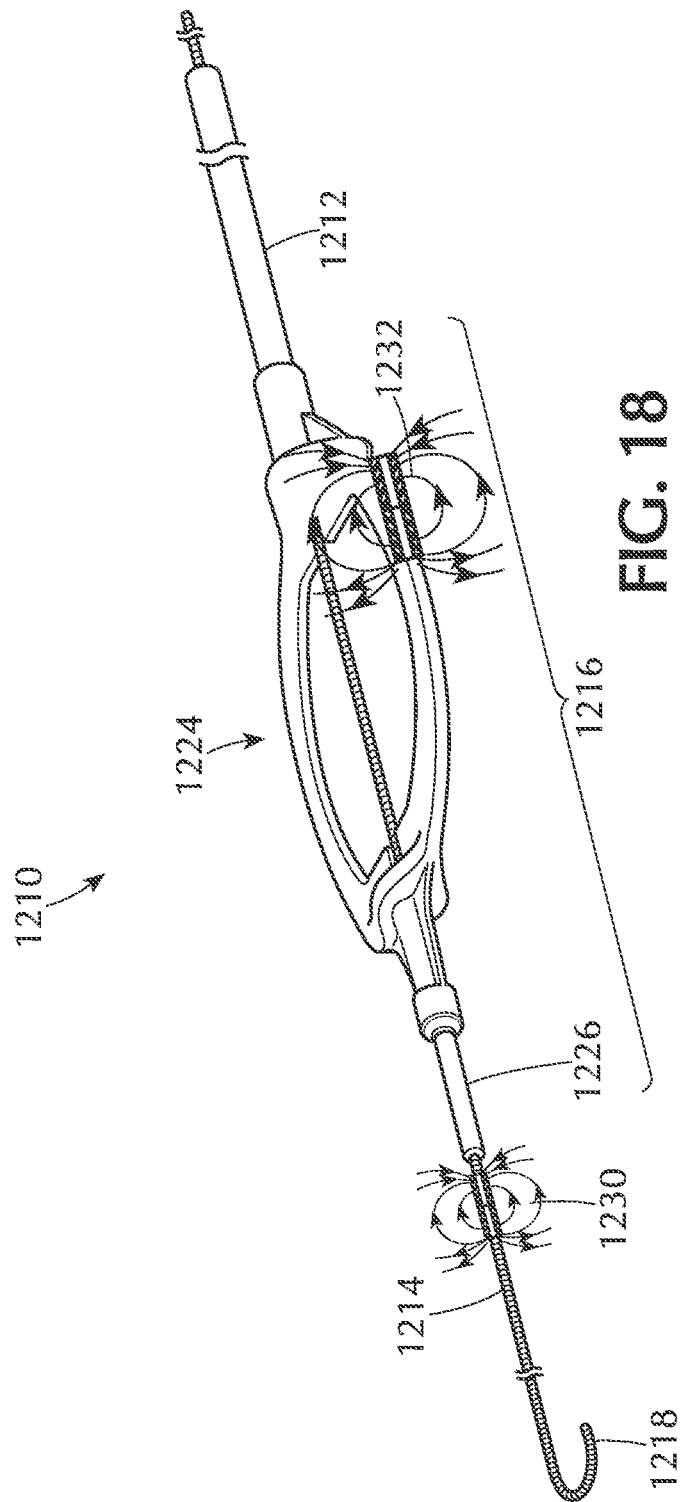
FIG. 18 shows an embodiment of a guidewire introducer assembly.

Referring now to FIG. 18, an embodiment of a medical device in the form a guidewire introducer assembly 1210 including a guidewire introducer subassembly 1216 having at least one end 1212 (a proximal end) and a main body 1224, a distal end 1226, and a guidewire 1214 including a distal end 1218 extending from one end of the guidewire introducer subassembly 1216. One of the guidewire introducer subassembly 1216 and the guidewire 1214 includes a permanent magnet element, and the other of the guidewire introducer subassembly and the guidewire includes a magnetizable feature. In the embodiment shown the guidewire 1214 include a permanent magnet element 1230 and the guidewire introducer subassembly includes the magnetizable element. In other embodiments, this configuration could be reversed where the magnetizable feature is on the guidewire, and the permanent magnet could be on the guidewire introducer subassembly.

The use of a permanent magnet element on the guidewire 1214 and a magnetizable feature on the guidewire introducer subassembly 1216 provides the ability to calculate the guidewire distal end 1218 or tip position based on known geometry relative to the position of magnetizable feature 1232 on guidewire introducer subassembly 1216 from which a calculated guidewire distal end 1218 or tip position can be determined. The permanent magnet element 1230 provides a static magnetic field, while the magnetizable feature 1232 on the guidewire introducer subassembly 1216 can be magnetized with an externally applied magnetic field prior to insertion of the guidewire 1214 into the patient.

The devices described with respect to FIGS. 15-18 can be utilized in methods and systems, similar to the system and method described with respect to FIG. 13. Thus, in an embodiment, a system for determining relative position of a catheter adapter subassembly and wire subassembly comprises a catheter having a catheter distal tip and a wire having a wire distal tip; a permanent magnet element associated with one of the catheter adapter subassembly and wire subassembly; a magnetizable feature associated with the other of the catheter adapter subassembly and the wire subassembly; and magnetometers positioned with respect to the catheter adapter subassembly and the wire subassembly, the magnetometers configured to determine relative movement of the catheter adapter subassembly and wire subassembly. In an embodiment, the permanent magnet or the magnetizable feature on a fixed location on the catheter adapter subassembly or wire subassembly provides a measurement datum to determine movement of the magnetizable feature and permanent magnet. In an embodiment, the permanent magnet is on the wire subassembly and the magnetizable feature is on the catheter adapter subassembly. In an embodiment, the permanent magnet is on the catheter adapter subassembly and the magnetizable feature is on the wire subassembly. In an embodiment, the magnetometers include three different magnetometers arranged in a three-dimensional grid array as part of an ultrasound system which can derive a three-dimensional correlation to obtain a distance from the grid array to the magnetizable feature or permanent magnet. In an embodiment, the three-dimensional correlation is determined by a function $I=f(B_i, \mu_r)$, where i=x or y or z along three axes, x, y and z are distances in three planes, B is a known magnetic field produced by the permanent magnet or magnetizable feature, and $\mu_r$ is magnetic permeability. In an embodiment, the correlation provides a distance in three planes to determine location of the catheter distal tip. In an embodiment, the correlation provides a distance in three planes to determine location of the wire distal tip.

Another embodiment pertains to a system for determining relative position of a needle subassembly and wire subassembly comprising a needle having a needle distal tip and a wire having a wire distal tip; a permanent magnet element associated with one of the needle subassembly and wire subassembly; a magnetizable feature associated with the other of the needle subassembly and the wire subassembly; and magnetometers positioned with respect to the needle subassembly and the wire subassembly, the magnetometers configured to determine relative movement of the needle subassembly and wire subassembly. In an embodiment, the permanent magnet or the magnetizable feature on a fixed location on the needle subassembly or wire subassembly provides a measurement datum to determine movement of the magnetizable feature and permanent magnet. In an embodiment, the permanent magnet is on the wire subassembly and the magnetizable feature is on the needle subassembly. In an embodiment, the permanent magnet is on the needle subassembly and the magnetizable feature is on the wire subassembly. In an embodiment, the magnetometers include three different magnetometers arranged in a three-dimensional grid array as part of an ultrasound system which can derive a three-dimensional correlation to obtain a distance from the grid array to the magnetizable feature or permanent magnet. In an embodiment, the three-dimensional correlation is determined by a function $I=f(B_i, \mu_r)$, where $i=x$ or y or z along three axes, x, y and z are distances in three planes, B is a known magnetic field produced by the permanent magnet or magnetizable feature, and $\mu_r$ is magnetic permeability. In an embodiment, the correlation provides a distance in three planes to determine location of the needle distal tip. In an embodiment, the correlation provides a distance in three planes to determine location of the wire distal tip.

Another aspect pertains to a method for determining a relative position of a catheter tip and a wire tip, the method comprising providing a catheter adapter subassembly including catheter and a wire subassembly including a wire, the catheter having a catheter distal tip and the wire having a wire distal tip; associating a permanent magnet element with one of the catheter and the wire; associating a magnetizable feature with the other of the catheter and the wire; obtaining a measured position of the permanent magnet; obtaining a measured position of the magnetizable feature to obtain a calculated position of the catheter distal tip and a calculated position of the wire distal tip; and comparing the calculated position of the catheter distal tip with the calculated position of the wire distal tip to determine the relative position of the catheter distal tip and the wire distal tip.

In an embodiment, the wire includes the magnetizable feature and the catheter includes the permanent magnet and the relative position of the catheter distal tip and the wire distal tip indicates that the catheter is properly seated on the wire. In an embodiment, the catheter adapter subassembly includes the magnetizable feature and the wire subassembly includes the permanent magnet, and relative movement of the catheter adapter subassembly and wire subassembly is determined by a three-dimensional array of magnetometers positioned in proximity to at least one of the permanent magnet the magnetizable feature. In an embodiment, the method further comprises magnetizing the magnetizable feature by applying an external magnetic field to the magnetizable feature. In an embodiment, the three-dimensional array of magnetometers is part of an ultrasound system, and the ultrasound system derives a three-dimensional correlation to obtain a distance from the array of magnetometers to the magnetizable feature or permanent magnet. In an embodiment, the three-dimensional correlation is determined by the function $I=f(B_i, \mu_r)$, where $i=x$ or y or z along three axes, x, y and z are distances in three planes, B is a known magnetic field produced by the permanent magnet or magnetizable feature, and $\mu_r$ is magnetic permeability. In an embodiment, the catheter adapter subassembly includes the permanent magnet and the wire subassembly includes the magnetizable feature, and relative movement of the catheter adapter subassembly and wire subassembly is determined by a three-dimensional array of magnetometers positioned in proximity to at least one of the permanent magnet the magnetizable feature.

In an embodiment, the method further comprises magnetizing the magnetizable feature by applying an external magnetic field to the magnetizable feature. In an embodiment, the three-dimensional array of magnetometers is part of an ultrasound system, and the ultrasound system derives a three-dimensional correlation to obtain a distance from the array of magnetometers to the magnetizable feature or permanent magnet. In an embodiment, the three-dimensional correlation is determined by the function $I=f(B_i, \mu_r)$, where $i=x$ or y or z along three axes, x, y and z are distances in three planes, B is a known magnetic field produced by the permanent magnet or magnetizable feature, and $\mu_r$ is magnetic permeability.

Another aspect pertains to a method for determining a relative position of a wire tip and a needle cannula tip, the method comprising providing a needle subassembly including needle and a wire subassembly including a wire, the needle having a needle distal tip and the wire having a wire distal tip; associating a permanent magnet element with one of the needle and the wire; associating a magnetizable feature with the other of the needle and the wire; obtaining a measured position of the permanent magnet; obtaining a measured position of the magnetizable feature to obtain a calculated position of the needle distal tip and a calculated position of the wire distal tip; and comparing the calculated position of the needle distal tip with the calculated position of the wire distal tip to determine the relative position of the needle distal tip and the wire distal tip. In an embodiment, the wire includes the magnetizable feature and the needle includes the permanent magnet and the relative position of the needle distal tip and the wire distal tip indicates that the needle is properly seated on the wire. In an embodiment, the needle subassembly includes the magnetizable feature and the wire subassembly includes the permanent magnet, and relative movement of the needle subassembly and wire subassembly is determined by a three-dimensional array of magnetometers positioned in proximity to at least one of the permanent magnet the magnetizable feature. In an embodiment, the method further comprises magnetizing the magnetizable feature by applying an external magnetic field to the magnetizable feature. In an embodiment, the three-dimensional array of magnetometers is part of an ultrasound system, and the ultrasound system derives a three-dimensional correlation to obtain a distance from the array of magnetometers to the magnetizable feature or permanent magnet. In an embodiment, the three-dimensional correlation is determined by the function $I=f(B_i, \mu_r)$, where $i=x$ or y or z along three axes, x, y and z are distances in three planes, B is a known magnetic field produced by the permanent magnet or magnetizable feature, and $\mu_r$ is magnetic permeability. In an embodiment, the catheter adapter subassembly includes the permanent magnet and the wire subassembly includes the magnetizable feature, and relative movement of the needle subassembly and wire subassembly is determined by a three-dimensional array of magnetometers positioned in proximity to at least one of the permanent magnet the magnetizable feature. In an embodiment, the method further comprises magnetizing the magnetizable feature by applying an external magnetic field to the magnetizable feature. In an embodiment, the three-dimensional array of magnetometers is part of an ultrasound system, and the ultrasound system derives a three-dimensional correlation to obtain a distance from the array of magnetometers to the magnetizable feature or permanent magnet. In an embodiment, the three-dimensional correlation is determined by the function $I=f(B_i, \mu_r)$, where $i=x$ or y or z along three axes, x, y and z are distances in three planes, B is a known magnetic field produced by the permanent magnet or magnetizable feature, and $\mu_r$ is magnetic permeability.

Although the disclosure herein provided a description with reference to particular embodiments, it is to be understood that these embodiments are merely illustrative of the principles and applications of the disclosure. It will be apparent to those skilled in the art that various modifications and variations can be made to the devices, methods and systems described in the of the present disclosure without departing from the spirit and scope thereof. Thus, it is intended that the present disclosure include modifications and variations that are within the scope of the appended claims and their equivalents.

What is claimed is:

1. A medical device configured to determine relative motion of a catheter tubing including a catheter tubing tip and a wire including a wire tip during intravenous insertion of the catheter tubing and the wire, the medical device comprising:
a guidewire introducer subassembly including a proximal end, a distal end and a main body and the catheter tubing extending from the main body and a wire subassembly including the wire, wherein one of the main body and the wire includes a permanent magnet element, and the other of the main body and the wire includes a magnetizable feature, the permanent magnet element configured to produce a known magnetic field at a given distance x through tissue of permeability $u_r$, and the magnetizable feature configured to produce a known magnetic field at a given distance x through tissue of permeability $u_r$, and relative motion of the wire and the catheter tubing when the wire is inserted in the catheter tubing during the intravenous insertion is measurable by a magnetometer which measures strength and direction of the magnetic field produced by the permanent magnet element and the magnetizable feature such that a position of the catheter tubing tip can be calculated based on a known geometrical relationship and dimensions of the guidewire introducer subassembly and the wire subassembly and placement of the permanent magnet element and the magnetizable feature, wherein one of the permanent magnet element and the magnetizable feature has a north pole and a south pole on axis with the main body and the other of the permanent magnet element and the magnetizable feature has a north pole and a south pole off axis with the main body and wherein the permanent magnet or the magnetizable feature is on a fixed location on the main body or the wire subassembly and provides a measurement datum to determine movement of the magnetizable feature and the permanent magnet.

2. The medical device of claim 1, wherein the guidewire introducer subassembly includes the magnetizable feature and the catheter tubing comprises magnetizable catheter tubing.

3. The medical device according to claim 1, wherein the wire includes the magnetizable feature and the main body includes the permanent magnet element, and the magnetizable feature of the wire is selected from the group consisting of an adhesive, the wire, a notch in the wire, a ferrule on the wire, and a spot weld on the wire.

4. The medical device according to claim 1, wherein the main body includes the permanent magnet element and the wire includes the magnetizable feature and the magnetizable feature is a magnetizable wire.

5. The medical device according to claim 1, wherein the wire subassembly includes the magnetizable feature, and the main body includes the permanent magnet element, wherein the permanent magnet element comprises a magnetic adhesive which attaches the catheter tubing to the main body.

6. A system configured to determine relative motion of a catheter tubing including a catheter tubing distal tip and a wire including a wire distal tip during intravenous insertion of the catheter tubing and the wire, the system comprising:
a guidewire introducer subassembly including a main body and the catheter tubing extending from the main body and a wire subassembly including the wire;
a permanent magnet element associated with one of the main body and the wire, the permanent magnet element configured to produce a known magnetic field at a given distance x through tissue of permeability $u_r$;
a magnetizable feature associated with the other of the main body and the wire, the magnetizable feature configured to produce a known magnetic field at a given distance x through tissue of permeability $u_r$; and
magnetometers positioned with respect to the main body and the wire, the magnetometers configured to determine relative movement of the catheter tubing distal tip and the wire distal tip during the intravenous insertion when the wire is inserted in the catheter tubing by measuring strength and direction of the magnetic field produced by the permanent magnet element and the magnetizable feature based on a known geometrical relationship and dimensions of the guidewire introducer subassembly and the wire subassembly and placement of the permanent magnet element and the magnetizable feature, wherein one of the permanent magnet element and the magnetizable feature has a north pole and a south pole on axis with the main body and the other of the permanent magnet element and the magnetizable feature has a north pole and a south pole off axis with the wire, and wherein the permanent magnet or the magnetizable feature is on a fixed location on the main body main body or the wire and provides a measurement datum to determine relative movement of the magnetizable feature and the permanent magnet.

7. The system of claim 6, wherein the permanent magnet is on the wire and the magnetizable feature is on the main body.

8. The system of claim 6 wherein the permanent magnet is on the main body and the magnetizable feature is on the wire.

9. The system of claim 6, wherein the magnetometers include three different magnetometers arranged in a three-dimensional grid array as part of an ultrasound system which can derive a three-dimensional correlation to obtain a distance from the grid array to the magnetizable feature or permanent magnet.

10. The system of claim 9, wherein the three-dimensional correlation is determined by a function $I=f(B_i \mu_r)$, where i=x or y or z along three axes, x, y and z are distances in three planes, B is a known magnetic field produced by the permanent magnet or magnetizable feature, and $u_r$ is magnetic permeability.

11. The system of claim 9, wherein the correlation provides a distance in three planes to determine location of the catheter distal tip.

12. The system of claim 9, wherein the correlation provides a distance in three planes to determine location of the wire distal tip.

13. The system of claim 6, wherein the guidewire introducer subassembly includes the magnetizable feature and the catheter tubing comprises magnetizable catheter tubing.

14. A method for determining a relative position of a catheter tubing including a catheter tubing distal tip and a wire including a wire distal tip during intravenous insertion of the catheter tubing and the wire, the method comprising:

providing a guidewire introducer subassembly and a wire subassembly, the guidewire introducer subassembly including a main body and the catheter tubing extending from the main body and the wire subassembly including the wire;

associating a permanent magnet element with one of the main body and the wire, the permanent magnet element configured to produce a known magnetic field at a given distance x through tissue of permeability $u_r$;

associating a magnetizable feature with the other of the main body and the wire, the magnetizable feature configured to produce a known magnetic field at a given distance x through tissue of permeability $u_r$;

obtaining a measured position of the permanent magnet;

obtaining a measured position of the magnetizable feature to obtain a calculated position of the catheter tubing distal tip and a calculated position of the wire distal tip when the wire is inserted in the catheter tubing;

during the intravenous insertion of the catheter tubing and the wire, comparing the calculated position of the catheter distal tip with the calculated position of the wire distal tip to determine the relative position of the catheter distal tip and the wire distal tip based on a known geometrical relationship and dimensions of the guidewire introducer subassembly and the wire subassembly and placement of the permanent magnet element and the magnetizable feature; and determining relative movement of the catheter tubing distal tip and the wire distal tip by measuring strength and direction of the magnetic field produced by the permanent magnet element and the magnetizable feature, wherein one of the permanent magnet element and the magnetizable feature has a north pole and a south pole on axis with the main body and the other of the permanent magnet element and the magnetizable feature has a north pole and a south pole off axis with the wire, and wherein the permanent magnet or the magnetizable feature is on a fixed location on the guidewire introducer subassembly or the wire subassembly and provides a measurement datum to determine relative movement of the magnetizable feature and the permanent magnet.

15. The method of claim 14, wherein the wire includes the magnetizable feature and the main body includes the permanent magnet and the relative position of the catheter tubing distal tip and the wire distal tip indicates that the catheter is properly seated on the wire.

16. The method of claim 14, wherein the main body includes the magnetizable feature and the wire subassembly includes the permanent magnet, and relative movement of the catheter tubing distal tip and the wire distal tip is determined by a three-dimensional array of magnetometers positioned in proximity to at least one of the permanent magnet the magnetizable feature.

17. The method of claim 16, further comprising magnetizing the magnetizable feature by applying an external magnetic field to the magnetizable feature.

18. The method of claim 16, wherein the three-dimensional array of magnetometers is part of an ultrasound system, and the ultrasound system derives a three-dimensional correlation to obtain a distance from the array of magnetometers to the magnetizable feature or permanent magnet.

19. The method of claim 18, wherein the three-dimensional correlation is determined by the function $I=f(B_i, u_r)$, where i=x or y or z along three axes, x, y and z are distances in three planes, B is a known magnetic field produced by the permanent magnet or magnetizable feature, and $u_r$ is magnetic permeability.

20. The method of claim 16, wherein the main body includes the permanent magnet and the wire includes the magnetizable feature, and relative movement of the catheter tubing distal tip and the wire distal tip is determined by a three-dimensional array of magnetometers positioned in proximity to at least one of the permanent magnet and the magnetizable feature.

21. The method of claim 20, further comprising magnetizing the magnetizable feature by applying an external magnetic field to the magnetizable feature.

22. The method of claim 20, wherein the three-dimensional array of magnetometers is part of an ultrasound system, and the ultrasound system derives a three-dimensional correlation to obtain a distance from the array of magnetometers to the magnetizable feature or permanent magnet.

23. The method of claim 22, wherein the three-dimensional correlation is determined by the function $I=f(B_i, u_r)$, where i=x or y or z along three axes, x, y and z are distances in three planes, B is a known magnetic field produced by the permanent magnet or magnetizable feature, and $u_r$ is magnetic permeability.

24. The method of claim 16, wherein the wire subassembly comprises a guidewire.

\* \* \* \* \*